United States Patent
Prammer et al.

(10) Patent No.: US 8,421,454 B2
(45) Date of Patent: Apr. 16, 2013

(54) HIGH-RESOLUTION WIRELINE NUCLEAR MAGNETIC RESONANCE TOOL

(75) Inventors: Manfred G. Prammer, Downingtown, PA (US); Sergey Knizhnik, Exton, PA (US); Clive D. Menezes, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 619 days.

(21) Appl. No.: 12/513,792

(22) PCT Filed: Dec. 15, 2006

(86) PCT No.: PCT/US2006/047974
§ 371 (c)(1),
(2), (4) Date: Dec. 2, 2009

(87) PCT Pub. No.: WO2008/073112
PCT Pub. Date: Jun. 19, 2008

(65) Prior Publication Data
US 2010/0182004 A1    Jul. 22, 2010

(51) Int. Cl.
*G01V 3/00* (2006.01)
(52) U.S. Cl.
USPC .......................................... 324/303; 324/300
(58) Field of Classification Search .......... 324/300–322; 72/7
See application file for complete search history.

(56) References Cited

U.S. PATENT DOCUMENTS

| | | | | |
|---|---|---|---|---|
| 5,757,186 A * | 5/1998 | Taicher et al. | | 324/303 |
| 5,814,988 A | 9/1998 | Itskovich et al. | | |
| 5,834,936 A * | 11/1998 | Taicher et al. | | 324/303 |
| 6,118,272 A * | 9/2000 | Taicher et al. | | 324/303 |
| 6,215,304 B1 | 4/2001 | Slade | | |
| 6,246,236 B1 | 6/2001 | Poitzsch et al. | | |
| 7,299,131 B2 * | 11/2007 | Tabarovsky et al. | | 702/7 |
| 7,834,622 B2 * | 11/2010 | Reiderman et al. | | 324/303 |
| 7,916,092 B2 * | 3/2011 | Homan et al. | | 343/719 |
| 2010/0179762 A1 * | 7/2010 | Tabarovsky et al. | | 702/7 |

FOREIGN PATENT DOCUMENTS

| WO | WO 2008/073112 A1 | 6/2008 |
|---|---|---|
| WO | WO-2008073112 A1 | 6/2008 |

* cited by examiner

*Primary Examiner* — Brij Shrivastav
(74) *Attorney, Agent, or Firm* — Schwegman Lundberg & Woessner, P.A.; Benjamin Fite

(57) ABSTRACT

A nuclear magnetic resonance well logging tool, where some embodiments comprise two, oppositely oriented magnets separated by a pole piece to guide static magnetic flux into a sensitive volume, and another pole piece serving as a core for several antennas. For some embodiments, the antennas are solenoids. Two of the antennas serve as transmit and receive antennas, where they are driven to generate an elliptically polarized magnetic field, and their antenna responses are combined so that the combined response is sensitive to elliptically polarized magnetic fields, but with zero gradient in the z-direction. A third antenna serves as a receive antenna sensitive to magnetic field vectors having a sinusoidal spatial variation in the z-direction of period equal to the length of the third antenna. A fourth antenna serves as a receive antenna sensitive to sinusoidal magnetic field vectors with the same spatial-frequency as the third antenna, but phase shifted by 90 degrees. A fifth antenna may be utilized, which serves as a receive antenna sensitive to the next higher spatial-frequency component of the received signal. The receive antennas have good cancellation of mutual coupling. Other embodiments are described and claimed.

32 Claims, 10 Drawing Sheets

HIGH-RESOLUTION WIRELINE NUCLEAR MAGNETIC RESONANCE TOOL

FIELD

The present invention relates to well logging, and more particularly, to a nuclear magnetic resonance well logging tool.

BACKGROUND

In the field of well logging, there is a clear need for high-resolution borehole measurements. Log analysis in general, and in particular the calculation of hydrocarbon saturations, are often based on induction measurements with an intrinsic resolution of 2 feet or worse. In an inhomogeneous reservoir with sand and or shale layers, the non-linear (current-seeking) nature of the induction measurement becomes evident. If the induced currents run parallel to the bed boundaries (measuring horizontal resistivity, Rh), then the electric currents tend to concentrate in the conductive shale layers, resulting in pessimistic estimates of hydrocarbon saturations when using traditional log analysis. Conversely, currents crossing bed boundaries encounter higher resistivities (vertical resistivity, Rv), sometimes resulting in overly optimistic estimates for hydrocarbon saturation. It is not trivial to reconcile Rh and Rv because shales exhibit different conductivities parallel to and normal to their compression direction. This extra free parameter would then need to be obtained from additional measurements, such as core analysis, which is often not available.

In general, well logging tool responses on a scale equal to or smaller than 2 feet may be considered high-resolution because such tools may be helpful in the disambiguation of mono-axial or tri-axial induction log responses. Electric and acoustic borehole images achieve this resolution, but such images are only available in a fraction of currently drilled holes, and are currently acquired only over limited sections. Oil-based mud poses significant challenges for electric borehole imaging, and an LWD (Logging While Drilling) oil-based imager is not, at this time, known to exist. The reconciliation of borehole imaging with induction measurements involves the summation of sand fractions to compute the net height of the hydrocarbon column over a given interval. Multiplying the net height by effective porosity, hydrocarbon saturation, and lateral area, gives (at least in theory) the total in-place hydrocarbon volume.

NMR (Nuclear Magnetic Resonance) measurements greatly streamline the calculation of hydrocarbon-in-place. As a linear measurement, NMR responds predictably to sand and or shale mixtures in arbitrary bedding and borehole geometries. For layered systems on scales less than the NMR resolution (2 to 4 ft), effective porosity from NMR represents the product ΦH (porosity Φ times column height H), bypassing the summation of individual layers. As a shallow measurement, NMR operates in the flushed or invaded part of the formation. Under irreducible conditions, the "movable" or "free" porosity determined by NMR in the flushed zone equals the porosity fraction available for hydrocarbon accumulation in the formation.

Classically, NMR porosity and irreducible water volume, BVI (Bulk Volume Irreducible), as determined from NMR, are used to derive a first-order estimate of formation permeability. This transform, the so-called Coates equation or the Timur-Coates equation, is highly nonlinear and is rooted in a distributed-shale model. It performs poorly in layered formations with characteristic scales smaller than the NMR resolution. In such formations, large flow volumes may be sustained by thin beds, resulting in high kH values (permeability k times column height H), while the Coates model predicts poor flow based on the large amounts of shale present. Thus, kH prediction from NMR should benefit immensely from improved vertical resolution.

Looking forward, convergence of the complementary features of tri-axial induction and NMR appears likely. One way to make a highly integrated NMR-plus-tri-axial induction evaluation work is for NMR to match at least the 2-foot induction resolution under arbitrary borehole and logging speed conditions. Preferably, NMR should also probe formation in-homogeneities in the 1-foot and ½-foot resolution range to de-convolve the induction response.

There are fundamental limits to borehole NMR arising from signal strength, thermal background noise, and the relaxation time, T1. These constraints led experimentally to a 2-foot antenna in the MRIL® Prime tool from Halliburton Energy Services, Inc. (MRIL®, Magnetic Resonance Imaging Logging, is an NMR wireline tool, and is a registered trademark of Halliburton Energy Services, Inc.) The signal from the antenna for the MRIL tool is averaged several times (stacked) to arrive at an acceptable signal-to-noise ratio (SNR). Depending on logging speed and the interval between measurements (constrained by T1), the vertical interval over which stacking occurs may reach several feet. Overall, the standard log resolution is about one-half (corresponding to 4 ft) of what would be achievable in a stationary measurement (2 ft). Reducing the antenna length provides no improvement in log resolution because the lower raw SNR requires more stacking The choice of a 2-foot aperture proved to be fortuitous with respect to measurements on hydrocarbons, which require that more-or-less the same measurement volume is available to measurements spaced 1-2 seconds apart. This requirement is met with the MRIL antenna at moderate logging speeds.

Schlumberger has developed a CMR (Combinable Magnetic Resonance) wireline logging tool that may be said to have a high-resolution flavor to it. The antenna for the CMR tool is only 6 inches tall, and requires a stacking depth of six to achieve an acceptable SNR. The instrument has only a single measurement volume, requiring either very long wait (idle) times between consecutive measurements, or a compromise with respect to under-calling porosity in free fluids. Typically, a reduction in CMR porosity is accepted to achieve reasonable logging speeds. The CMR tool is often run with pre-set wait times tuned to an anticipated logging speed such that measurement volumes are stacked toe-to-head, which alleviates the need to wait out full magnetization recovery. In this mode, vertical resolution is six times 6 inches, or 3 ft, which yields a resolution similar to the MRIL Prime tool.

Although the MRIL Prime and CMR tools have radically different designs, they nevertheless have similar vertical resolutions due to basic physical constraints. This is illustrated in FIG. 1, where various relative responses to a hypothetical chirp formation are computed. The chirp is shown by the top trace, labeled 102. Classically, a chirp is a signal having a linearly time-varying instantaneous frequency, so that as time increases, its instantaneous frequency increases. Because the tools are assumed to be moving at constant velocity, the distance traveled by a tool is proportional to time, so that the x-axis in FIG. 1 may be expressed as the distance that the tool has moved since the beginning of the chirp. Note that at the right margin of FIG. 1, the chirp has the highest spatial frequency, corresponding to having a high value for 3 inches of travel, followed by a low value for 3 inches of travel. For clarity, noise effects have been omitted.

The second trace from the top, labeled 104 in FIG. 1, shows the computed MRIL response, and the third trace from the top, labeled 106, is the CMR response. They are similar due to the amount of stacking required. The bottom trace, labeled 108, shows the CMR in BVI-only mode, which enables much faster sampling. In this mode, the CMR may double its vertical resolution.

Schlumberger's next-generation NMR wireline logging tool is referred to as an MR Scanner, and has three antennas in different tool sections: The main antenna is closely modeled after the MRIL tool and its side-looking version, the MRIL-XL tool, another tool from Halliburton Energy Services, Inc. Two auxiliary antennas on the MR Scanner provide a CMR-style measurement with 4-inch antenna apertures. It is claimed that stacking of these signals is not necessary, and that in operation the high-resolution antennas are fired every 5 inches. Therefore, assuming a single phase-alternated pair, these antennas may potentially deliver 1-foot log resolution. This may be true in vertical, smooth boreholes, but in deviated, rugose boreholes, we believe it is more likely that the solid, long tool body of the MR Scanner tool will force the high-resolution antennas off the borehole wall, resulting in a distorted measurement that is influenced by borehole mud.

A more robust measurement would be highly desirable, i.e., with a distance between tool face and sensitive volume of at least 2 inches instead of 1 inch as provided by the MR Scanner. It would be useful for such a tool to integrate with existing porosity tools, and to replace them wherever the use of chemical sources is not feasible. It would be desirable for the primary tool response to match the induction response on a length scale of 2 feet at any logging speed. Furthermore, it would be desirable for such a tool to probe the 12-inch, 6-inch and 3-inch scales for de-convolution of mono-axial and tri-axial induction logs, as well as improved kM estimates. Also, it would be desirable for the measurements to be independent of borehole angle, and robust against moderate borehole rugosity.

It is believed that consistent NMR log responses matched to the induction resolution would enable tightly integrated answer products, and a new understanding of the formation under investigation. NMR responses with better resolution than induction would feed into the real-time modeling of the induction response, by stabilizing the under-determined inverse induction problem. As a stand-alone answer product, we expect improvements in permeability estimates by orders of magnitude where currently the simple distributed-shale model does not match the sand-shale bedding reality. An integrated answer product would use both the high-resolution NMR information and the tri-axial induction data to estimate formation producability relative to borehole orientation and placement.

DESCRIPTION OF EMBODIMENTS

In the descriptions that follow, the scope of the term "some embodiments" is not to be so limited as to mean more than one embodiment, but rather, the scope may include one embodiment, more than one embodiment, or perhaps all embodiments.

Figure 2:
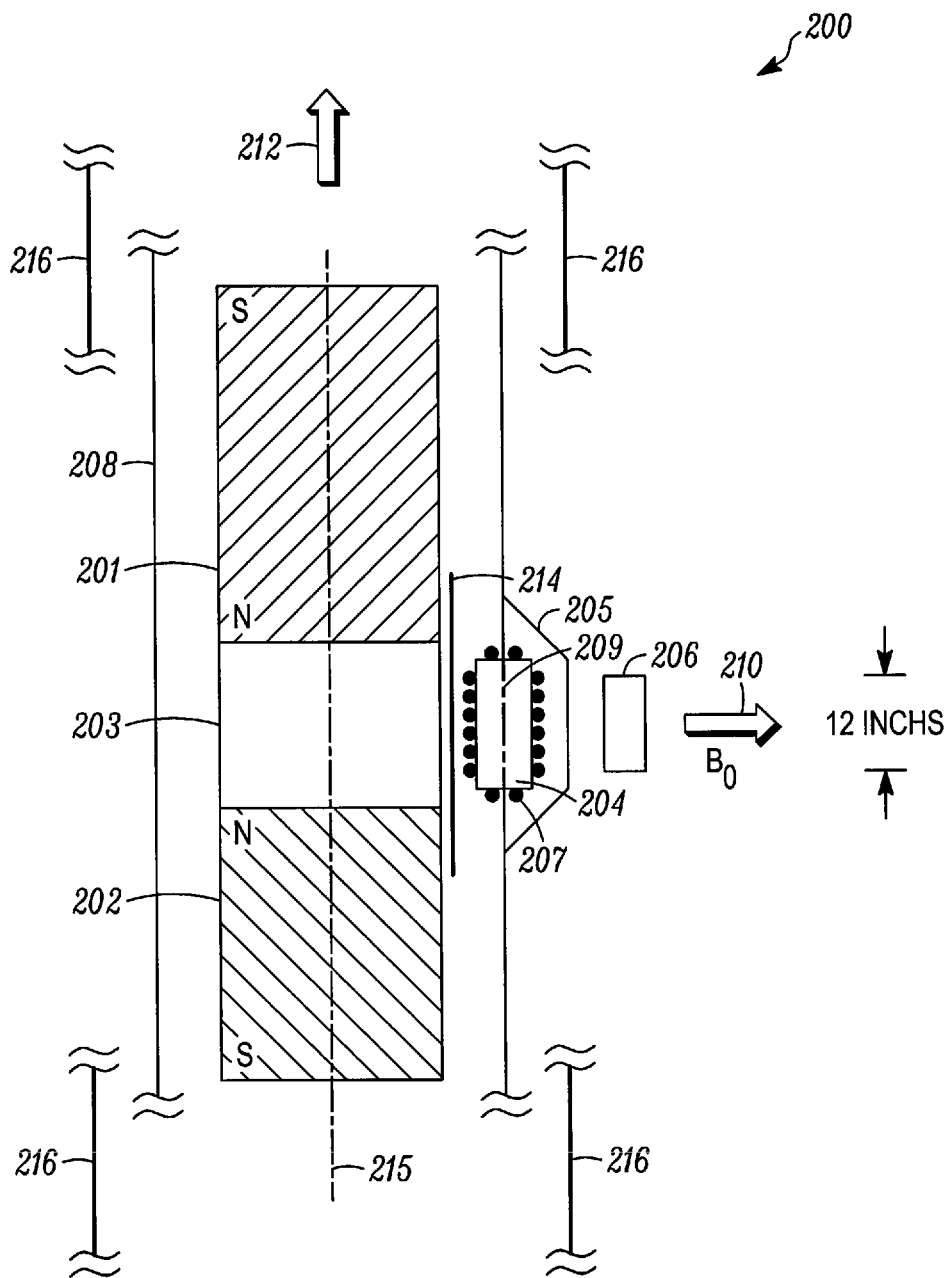
FIG. 2 illustrates an NMR logging tool according to an embodiment of the present invention.

FIG. 2 illustrates a cross-sectional plan view of a portion of tool 200 according to an embodiment of the present invention. Much of the structure of tool 200 is for the most part symmetrical about some axis, which for convenience is labeled 215. Arrow 212 indicates the logging direction for tool 200. For the most part, axis 215 is parallel to borehole 216.

Two magnets, 201 and 202, are housed in pressure housing 208. Magnets 201 and 202 are oriented to have like poles facing each other. That is, the internal magnetization of magnets 201 and 202 along their axes (axial magnetization) are for the most part parallel to axis 215, but directed oppositely. For the particular embodiment in FIG. 2, the north poles of magnets 201 and 202 are facing each other, that is, they are proximal to each other. In other embodiments, the south poles may be facing each other.

Pole piece 203 is proximal to magnets 201 and 202, and pole piece 204 is proximal to pole piece 203. Proximal does not necessarily mean adjacent, for there may be other component structures in-between two proximal components. These pole pieces may be constructed from soft-magnetic material, having a relatively high magnetic permeability, so that the static magnetic flux due to magnets 201 and 202 is directed out of tool 200 into a formation (not shown). The sensitive volumes to be measured are for the most part sections of cylindrical rings. A sensitive volume of the formation to be measured is indicated as a simplified and idealized plan view labeled 206. For some embodiments, sensitive volume 206 may be approximately 2 inches from the face of pole piece 204, and approximately 12 inches tall. Arrow 210 depicts the direction of the static magnetic vector field in sensitive volume 206, where the static magnetic vector field is denoted as $B_0$. Within sensitive volume 206, the static magnetic vector field $B_0$ is generally directed radially outwards, relative to the borehole.

For some embodiments, pole pieces 203 and 204 may be integrated into a single pole piece. In other embodiments, pole piece 204 may surround pole piece 203. In other embodiments, pole piece 204 may be embedded in skid 205 having a non-metallic window that rides on the borehole wall. A non-metallic window allows RF (Radio Frequency) energy to propagate to sensitive volume 206. Preferably, pole piece 204 does not saturate at the permanent field produced by magnets 210 and 202. Passive tool orientation devices, well known in the art, may be employed to ensure borehole wall contact. In a slick bore configuration, the window in skid 205 defines which side needs to point towards the borehole wall.

Pole piece 204 guides the static magnetic flux. In addition, pole piece 204 serves as a core for the RF antennas, and concentrates the RF field lines toward sensitive volume 206. For some embodiments, the RF antennas are solenoids having pole piece 204 as a core. A very simplified, cross-sectional plan view of the windings making up the solenoids is indicated by the solid dots surrounding pole piece 204, where as an example one of these solid dots is labeled 207. These solenoids each have an axis. All but one of the solenoids have axes parallel to each other, which are collectively indicated by axis 209. The axis for one of the solenoids is perpendicular to axis 209, lying in the plane of the drawing, but for simplicity is not shown. These solenoids are better described by referring to FIG. 3, discussed later.

A windowed magnetic shield comprised of a highly conductive material, such as copper, may be arranged around 204 to focus the RF flux towards the sensitive volume 206, and to exclude the RF flux from the interior of tool 200 and from the backside of tool 200 that is exposed to the borehole. Solid line 214 represents a simplified, cross-sectional plan view of a section of such a shield.

Figure 3:
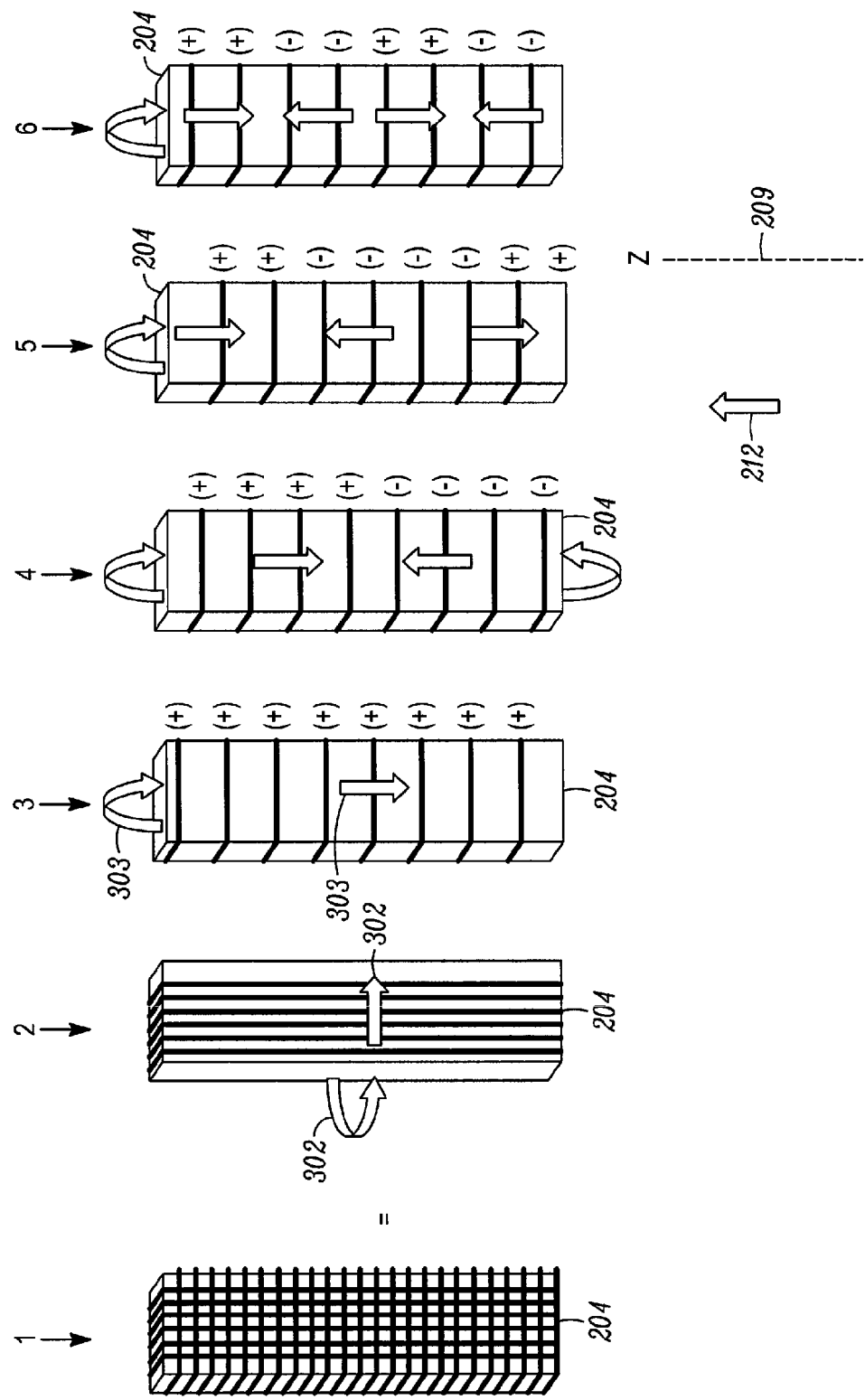
FIG. 3 illustrates in more detail the antennas employed in the embodiment of FIG. 2.

FIG. 3 provides a simplified perspective view of the solenoids making up the various RF antennas in tool 200 according to an embodiment of the present invention. The combination of pole piece 204 with the RF antennas is labeled 1 in FIG. 3, and for ease of illustration, pole piece 204 is replicated 5 more times in FIG. 3, with labels 2 through 6. Each replica 2 through 6 of pole piece 204 illustrates an antenna (or solenoid). For convenience, we may use the terms antenna and solenoid interchangeably. The equality symbol in FIG. 3 pictorially indicates that for embodiments represented by FIG. 3, each solenoid shown in replicas 2 through 5 is present in the combination of antennas shown in replica 1. In the discussion that follows, each label 2 through 5 is also used to label the particular antenna (solenoid) illustrated in the correspondingly labeled replica.

For clarity, not all of the windings making up any particular solenoid are shown in FIG. 3. For example, only 6 windings are explicitly drawn for solenoid 2, and only 8 windings are explicitly drawn for the remaining solenoids. However, in practice, there may be different numbers of turns for each solenoid. For some embodiments, core 204 is approximately 12 inches tall by 3 inches wide by 1 inch deep. For reference, dashed arrow 209 indicates the axis direction of solenoids 3 through 6, where arrow 212 indicates logging direction. Axis 209 will all be referred to as the z-axis, or z-direction, and is labeled as such in FIG. 3.

Antenna 2 comprises a solenoid having longitudinal windings. That is, for the most part, the windings are along the direction of axis 209, so that its solenoid axis is perpendicular to axis 209. Arrows 302 illustrate example momentary directions of the RF magnetic field vectors for solenoid 2. The actual directions alternate with the frequency of the current driving solenoid 2. For the most part, the RF magnetic field vectors passing through the sensitive volume lie in planes perpendicular to axis 209. Relative to FIG. 2, within the sensitive volume 206, the magnetic RF field vectors are substantially perpendicular to the direction of the radially oriented B0 field, 210.

Antenna 3 comprises a solenoid having tangential windings, that is, windings that are for the most part lie in planes perpendicular to axis 209. Of labeled arrows 303, the straight arrow 303 illustrates an example momentary direction of magnetic RF field for solenoid 3 in sensitive volume 206, where it is seen that for the most part this RF field is parallel to axis 209, and perpendicular to the radially oriented $B_0$ field.

During operation of tool 200, the current driving solenoid 2 and the current driving solenoid 3 are quadrature to each other. That is, the currents differ by a 90° phase shift. As a result, within sensitive volume 206, solenoids 2 and 3 together generate an elliptically polarized magnetic field, and in particular, may generate a circularly polarized magnetic field. A circularly polarized magnetic field is more efficient in exciting nuclear resonance than a linearly polarized magnetic field. This is so because protons may be thought of as being right-handed in the sense that they resonate only with a field vector that matches their intrinsic spin direction. That is, protons have a right handed chirality. Because a linearly polarized field may be decomposed into a right-handed circularly polarized field and a left-handed circularly polarized field, one-half of the power carried by a linearly polarized field does not match the intrinsic spin, and is wasted. During reception, the received signals from antennas 2 and 3 are phase-shifted, in the time domain, by 90° relative to each other, and then summed.

Because antennas 2 and 3 are driven in a quadrature relationship to each other, given the constraint of an available peak output power, the quadrature current pulses driving antennas 2 and 3 may be raised by a factor of $\sqrt{2}$ compared to the case of driving antennas 2 and 3 in phase. The pulse duration may then be shortened, while keeping the time-integral of the pulse constant. Using shorter pulses results in increased bandwidth, which is an advantage in a magnetic field having a non-zero gradient, as employed in NMR borehole tools. In a magnetic field having a gradient, the higher bandwidth results in a larger sensitive volume, and therefore a higher received signal. Although the noise level increases as well due to a higher bandwidth, there is a net gain in SNR. The combined effects of a wider bandwidth, reduced pulse spacing during transmission, and dual-channel reception are roughly equivalent to threefold stacking.

We expect that the SNR obtained from this arrangement is high enough that with one more stacking operation, forming a phase-alternated pair, acceptable log quality is achieved. In some embodiments, where the solenoid heights are each 12 inches, antennas 2 and 3 fire simultaneously every time tool 200 moves 12 inches. The z-axis (borehole axis) position data may be derived from short-term integration of z-axis acceleration. For some embodiments, every measurement volume is used only once, so that the logging speed and relaxation time T1 are effectively decoupled. A remaining constraint on logging speed is the length of leading magnet 201, because the formation should be exposed to the magnetic field for a multiple of T1.

Antennas 4, 5, and 6 are receive antennas to provide high-resolution information during reception, and for some embodiments are only used during reception in a linearly polarized mode. These antennas should not interfere with the operation of the main antennas, antennas 2 and 3, and should not couple magnetically with each other.

In FIG. 3, for each antenna 3 through 6, the symbols (+) and (−) next to the displayed solenoid windings making up an antenna indicate the momentary phase of emf (electro-motive force) induced by an NMR signal in that section of the solenoid so labeled. Based on the reciprocity principle, these symbols may be viewed as the momentary directions of the RF magnetic field induced in the sensitive volume by the corresponding section of the solenoid if the latter is used as a transmitter antenna.

For example, each displayed winding in solenoid 3 has next to it the same symbol, namely (+), denoting that the contributions to the total induced emf contributed by the windings are in phase with respect to each other. Stated alternatively, when used as a transmit antenna, the contributions of each winding to the magnetic field in the sensitive volume are in phase with respect to each other. Yet another way to view this feature is, if direct current were to flow through solenoid 3, then the direction of direct current flowing in each winding has the same sense, either clockwise or counter-clockwise, relative to the axis of the solenoid. This feature may physically be realized by simply forming the solenoid so that each winding is wound in the same direction about pole piece 204.

Solenoid 4, for example, is a solenoid in which the top-half displayed windings each have a (+) next to them, and the bottom-half displayed windings each have a (−) next to them. Thus, the emf contribution to the total received NMR signal from the top-half section of solenoid 4 is opposite in sign to that of the bottom-half section, assuming that the sensitive volume is uniformly excited. For an embodiment in which pole piece 204 is approximately 12 inches high, the heights of each section may be 6 inches.

The oppositely induced emf NMR signals for the two halves of solenoid 4 may be physically realized in various ways. One way is for the direction of windings for the top-half of solenoid 4 to be opposite that of the bottom-half. For example, if when looking down into the borehole (opposite the direction implied by 212) the top-half of solenoid 4 has windings wound in some direction, say the clockwise direction, then the bottom-half of solenoid 4 has windings wound in the counter-clockwise direction.

As another example of how solenoid 4 may be formed, all windings may be wound having the same sense of direction, but where the two-halves of the solenoid are electrically connected in such a way that they contribute oppositely phased emfs. One way to describe such an embodiment is to imagine that solenoid 4 comprises two solenoids, a top solenoid and a bottom solenoid, each wound in the same direction, but where the bottom end conductor of the top solenoid is connected to the bottom end conductor of the bottom solenoid. The two ends of the resulting solenoid are then the top end conductor of the top solenoid and the top end conductor of the bottom solenoid.

Solenoid 5 comprises three sections, where the top section has the same emf phase as the bottom section, but of opposite phase to that of the middle section. This is indicated in FIG. 3 by showing two displayed windings in the top section, each having a (+) symbol next to them, and two displayed windings in the bottom section, each having a (+) symbol next to them. The middle section has four displayed windings, each having a (−) symbol next to them. Thus, for the embodiment of FIG. 3, the relative ratio of windings among the three sections of solenoid 5 is 1:2:1. For an embodiment in which pole piece 204 is approximately 12 inches high, the heights of the top, middle, and bottom groups of windings are, respectively, 3 inches, 6 inches, and 3 inches.

Solenoid 6 comprises four sections, where the emf phases alternate from one section to the next, as indicated in FIG. 3. Solenoid 6 is drawn in FIG. 3 to indicate that each section has essentially the same height, so that for an embodiment in which pole piece 204 is approximately 12 inches high, the height of each section is 3 inches.

In some embodiments, operation of the antennas may be divided into two modes, where for one mode, referred to as mode A, sensitive volume 206 is excited by antennas 2 and 3, and antennas 2 through 6 are used for reception, and for the other mode, referred to as mode B, sensitive volume 206 is excited by antennas 2 and 3, and antennas 2 through 5 are used for reception.

Antennas 2 through 6 are sensitive to different spatial frequencies of the formation. Solenoid 2 has a single magnetic moment direction, and solenoid 3 has a single magnetic moment direction orthogonal to that of solenoid 2. During the receive mode, for a time-sinusoidal magnetic field with zero spatial gradient, the current induced in each winding of solenoid 2 is in phase with each other, and similarly for solenoid 3. As a result, solenoids 2 and 3 are sensitive to the DC ("direct current", or non-time-varying) components of the received magnetic field.

Antennas 4 and 5 are sensitive to periodic signals having the same spatial-frequency in z-axis 209, but for which the phase difference of the two periodic signals is 90°. This may be observed by repeating antennas 4 and 5 along the z-axis. If L denotes the length of each antenna, then repeating the antennas yields a periodic pattern of solenoids, of period L, in which the dominant spatial-frequency component for each of the repeating patterns has a spatial-frequency, in radians, of $2\pi/L$ (a period of L). Without loss of generality, the origin of the z-axis may be chosen so that the dominant (largest-in-magnitude) term in the Fourier series expansion for antenna 4 repeated (stacked in the z-axis direction) is $A \sin[(2\pi)(z/L)]$, where A is a scale factor. Then, with this choice of origin, the dominant (greatest-in-magnitude) term in the Fourier series expansion for antenna 5 repeated in the z-dimension is $A \cos[(2\pi)(z/L)]$.

For an embodiment in which the solenoids making up antennas 4 and 5 are each 12 inches high, antenna 4 may be viewed as being sensitive to the "sine" component of 1-foot periodic signals, and antenna 5 may be viewed as being sensitive to the "cosine" component of 1-foot periodic signals.

Because the alignment between tool 200 and the formation layers is random, it is preferable to acquire both the "sine" and "cosine" components.

Antenna 6 is sensitive to the next-higher spatial-frequency components. That is, for a solenoid of length L, the dominant component in the Fourier series expansion has a spatial-frequency of $4\pi/L$.

It should be appreciated that the antennas are, of course, not repeated indefinitely. One may view a single antenna as a repeated antenna weighted (multiplied) by a window of length equal to the length of the solenoid, L. As is well known, multiplication in the spatial domain is a convolution in the spatial-frequency domain, so that more than one Fourier component comes into play. That is, for example, although antennas 4 and 5 have an antenna response having Fourier components $A \sin[(2\pi)(z/L)]$ and $A \cos[(2\pi)(z/L)]$, respectively, they also will have other Fourier components at other spatial-frequencies, but with decreasing magnitude. Accordingly, that is the reason for using the qualifier dominant, or greatest-in-magnitude, when referring to the various Fourier components of the various antenna responses. That is, the dominant, or greatest-in-magnitude, Fourier components for antennas 4 and 5 are, respectively, $A \sin[(2\pi)(z/L)]$ and $A \cos[(2\pi)(z/L)]$.

It should be appreciated that the expansion of the various antenna responses along the spatial z-axis 209 is valid over a length L along spatial z-axis 209, but it is not to be implied that the Fourier series represents the various antenna responses for a length greater than L. That is, a spatial antenna response A(z) written as the Fourier series $$A(z) = \sum_n F(n) \exp(jn 2\pi z / L),$$

where the individual terms $F(n)\exp(jn2\pi z/L)$ are the Fourier components, is only meant to be valid for $z \in [0,L]$, where for simplicity the sensitive volume is bounded by z=0 and z=L.

It should be appreciated that only the spatial part of the antenna responses have been discussed, and that the time-varying nature of the signals were not discussed in detail. That is, the Fourier series discussed above are transformations from the spatial domain to the spatial-frequency domain. But there is also a time component to the antenna responses. In its simplest form, this time response is a sinusoid at the resonance frequency of the sensitive volume. In practice, there is some spread to the frequency because the signals are of finite time duration, as well as other factors.

It should be appreciated that the symbols (+) and (−) for a particular solenoid indicate the emf phases for the sections of the particular solenoid, and does not necessarily indicate a relationship between one solenoid and another. For example, in the particular embodiment of FIG. 3, the same symbol (+) is used for the top-half section of solenoid 4 and for all the windings of solenoid 3. But that does not necessarily mean that during reception, the emf induced in the top-half section of solenoid 4 is in phase with the emf induced in solenoid 3. The windings of the solenoids for these two antennas could be such that the induced currents are 180° out of phase with respect to each other. If this is not desirable, then during signal processing, either in the analog domain or the digital domain, a received signal may be phase shifted by 180°.

With the various sections of the receive solenoids 3, 4, 5, and 6 wound as indicated in FIG. 3, there is ideally no mutual coupling among solenoids 3, 4, 5, and 6. When a DC current flows through solenoid 3, the current contributes to a single magnetic moment direction. When a DC current flows through solenoid 4, the top and bottom sections each contribute a magnetic moment having the same magnitude, but having opposite directions. Solenoids 3 and 4 are aligned to have the same axis, wound around the same pole piece. In this way, when a current is injected into solenoid 3, the magnetic flux through solenoid 4 due to the current injected into solenoid 3 induces a net zero voltage. That is, if one writes the magnetic vector in solenoid 4 due to current injected into solenoid 4 as $\overline{B}_{3,4}$, then $$\iint \overline{B}_{3,4} \cdot dA_T = -\iint \overline{B}_{3,4} \cdot dA_B,$$

where the integration on the left hand side of the above-displayed equation is over the top section of solenoid 4, and the integration on the right hand side is over the bottom section. (The above notation is standard, where in general dA is an element of area with direction given by the right-hand-screw rule applied to a direction along a loop bounding the area of integration.)

The above equality follows easily if one assumes that $\overline{B}_{3,4}$ is uniform inside solenoid 4, and that the windings for solenoid 4 have the same pitch. The change in sign for the top-half and bottom-half integrations is due to the change in the winding directions for the top-half and bottom-half sections of solenoid 4. For example, a particular direction may be chosen for a closed loop, where the closed loop contains the wire making up solenoid 4. The directions for $dA_T$ and $dA_B$ then follow from the so-called right-hand-screw rule, and it is easily observed that the direction for $dA_T$ is opposite that of $dA_B$ at corresponding points in an integration surface. The result is that the total flux, sometimes referred to as flux linkage, integrated over all of the turn-areas of solenoid 4 due to current injected into solenoid 3 is zero. That is, $$\iint \overline{B}_{3,4} \cdot dA = \iint \overline{B}_{3,4} \cdot dA_T + \iint \overline{B}_{3,4} \cdot dA_B = 0$$

Similarly, the total flux integrated over all of the turn-areas of solenoid 3 due to current injected into solenoid 4 is also zero.

When a DC current flows through solenoid 5, the top-half and bottom-half sections of solenoid 5 contribute magnetic moments having the same magnitude and same direction, and the middle section contributes a magnetic moment having twice the magnitude as the top and bottom halves, but of opposite direction. If a current is injected into solenoid 3, the magnetic flux linkage in solenoid 5 satisfies the relationship, $$\iint \overline{B}_{3,5} \cdot dA_T = -\frac{1}{2} \iint \overline{B}_{3,5} \cdot dA_M = \iint \overline{B}_{3,5} \cdot dA_B,$$

where the first integration is over the top section of solenoid 5 labeled with (+), the middle integration is over the middle section of solenoid 5 labeled with (−), and the last integration is over the bottom section of solenoid 5 labeled with (+). The ½ appears because the middle section of solenoid 5 contributes twice the induced voltage as the top and bottom sections. In the embodiment of FIG. 3, this feature is realized by keeping the same pitch for the windings in solenoid 5, and having twice as many windings for the middle section as the top and bottom sections. The result is that an injected current in solenoid 3 induces a net zero voltage in solenoid 5. Similarly, an injected current in solenoid 5 induces a net zero voltage in solenoid 3.

When a current is injected into solenoid 4, the flux linkage in the middle section of solenoid 5 is zero. This follows because the magnetic field $\overline{B}_{4,5}$ in the middle section of solenoid 5 changes direction halfway through the middle section. That is, $$\iint \overline{B}_{4,5} \cdot dA_M = 0$$

Note that, essentially, $dA_T$ and $dA_B$ have the same direction for both the top and bottom sections of solenoid 5, but that $\overline{B}_{4,5}$ changes direction for the top and bottom sections. As a result, $$\iint \overline{B}_{4,5} \cdot dA_T = -\iint \overline{B}_{4,5} \cdot dA_B,$$

and it follows that $$\iint \overline{B}_{4,5} \cdot dA = 0,$$

so that the flux linkage in solenoid 5 due to an injected current in solenoid 4 is zero, resulting in a net zero induced voltage. Similarly, when a current is injected into solenoid 5, there is a net zero induced voltage in solenoid 4.

When a DC current flows through solenoid 6, each section in solenoid 6 contributes a magnetic moment having the same magnitude, where the magnetic moments for the first and third sections (counting from the top) have the same direction, and the magnetic moments for the second and fourth sections have the same direction, but opposite to that of the first and third sections. When a current is injected into solenoid 3, the magnetic fluxes in solenoid 6 satisfy the relationship $$\iint \overline{B}_{3,6} \cdot dA_1 = -\iint \overline{B}_{3,6} \cdot dA_2 = \iint \overline{B}_{3,6} \cdot dA_3 = -\iint \overline{B}_{3,6} \cdot dA_4,$$

where the successive integrations in the above-displayed equation refer to the successive sections of solenoid 6. As a result, the total net voltage induced in solenoid 6 is zero. Similarly, the induced voltage in solenoid 3 due to an injected current in solenoid 6 is zero.

Similar arguments may be made to the flux linkages in solenoid 6 due to injected currents in solenoids 4 and 5. The result is that injected currents in either solenoids 4 or 5 induce a zero voltage in solenoid 6, and an injected current in solenoid 6 induce zero voltages in solenoids 4 and 5.

The zero mutual coupling may be expressed as $$\iint \overline{B}_{i,j} \cdot dA = 0, \text{ for } i \neq j,$$

where $\overline{B}_{i,j}$ is the magnetic field vector in solenoid j due to current in solenoid i, and the integration is performed over solenoid j. One may define an inductance matrix $\overline{L}$, where $$\overline{v} = \overline{L}\frac{d\overline{i}}{dt},$$

where $\overline{v}$ is a voltage whose components are the induced voltages in the solenoids, and $\overline{i}$ is a vector whose components are the injected currents in the corresponding solenoids. Then, zero mutual coupling may be expressed by stating that the inductance matrix $\overline{L}$ is a diagonal matrix.

In practice, the above expressions for flux linkages are not satisfied exactly. There will always be some degree of mutual coupling due to imperfect windings, imperfect symmetries, and adjacent conductors. But it is to be understood that the receive antennas may be designed so as to mitigate mutual coupling. This may be facilitated by tuning. For example, metal-tipped screws with nylon shafts may be used, where the screws move in and out of the pole piece over which the solenoids are wound. By moving the screws in or out, fine tuning may be accomplished to mitigate mutual coupling.

The degree of mutual coupling still present after tuning may be expressed as a ratio of flux linkages. That is, the previously displayed expression for zero mutual coupling may be modified to $$\frac{\iint \overline{B}_{i,j} \cdot dA}{\iint \overline{B}_{i,i} \cdot dA} \leq M \text{ for } i \neq j,$$

where M sets an upper bound for the degree of mutual coupling. The denominator in the above expression is the total flux linkage in solenoid i due to current injected in solenoid i, and may be termed the self flux linkage of solenoid i. The numerator may be termed a mutual flux linkage. It is expected that embodiments may achieve an M of approximately −10 dB (decibels) or better. (In this context, xdB is $20\log_{10}(x)$.) With proper manufacturing and tuning, it is expected that embodiments should be able to achieve an M of approximately −20 dB.

The above expression for mutual coupling may also be re-worded as a ratio of the off-diagonal elements of the inductance matrix $\overline{L}$ to the diagonal elements. That is, one may write $$\frac{\overline{L}_{i,j}}{\overline{L}_{j,j}} \leq M, \text{ for } i \neq j.$$

By minimizing mutual coupling, better resolution is obtained. Mutual coupling allows noise induced in one coil to induce correlated noise in another. By minimizing mutual coupling, the noise induced in one coil tends to be uncorrelated with the noise induced in another, thereby providing a larger signal-to-noise ratio when signal processing is applied.

The illustration of the antennas in FIG. 3 is not meant to imply a spatial ordering of the antennas in an embodiment. That is, antenna 4 is not necessarily wound about pole piece 204 after antenna 3 has been wound about pole piece 204; antenna 5 is not necessarily wound about pole piece 204 after antenna 4 has been wound; and so forth.

Figure 4:
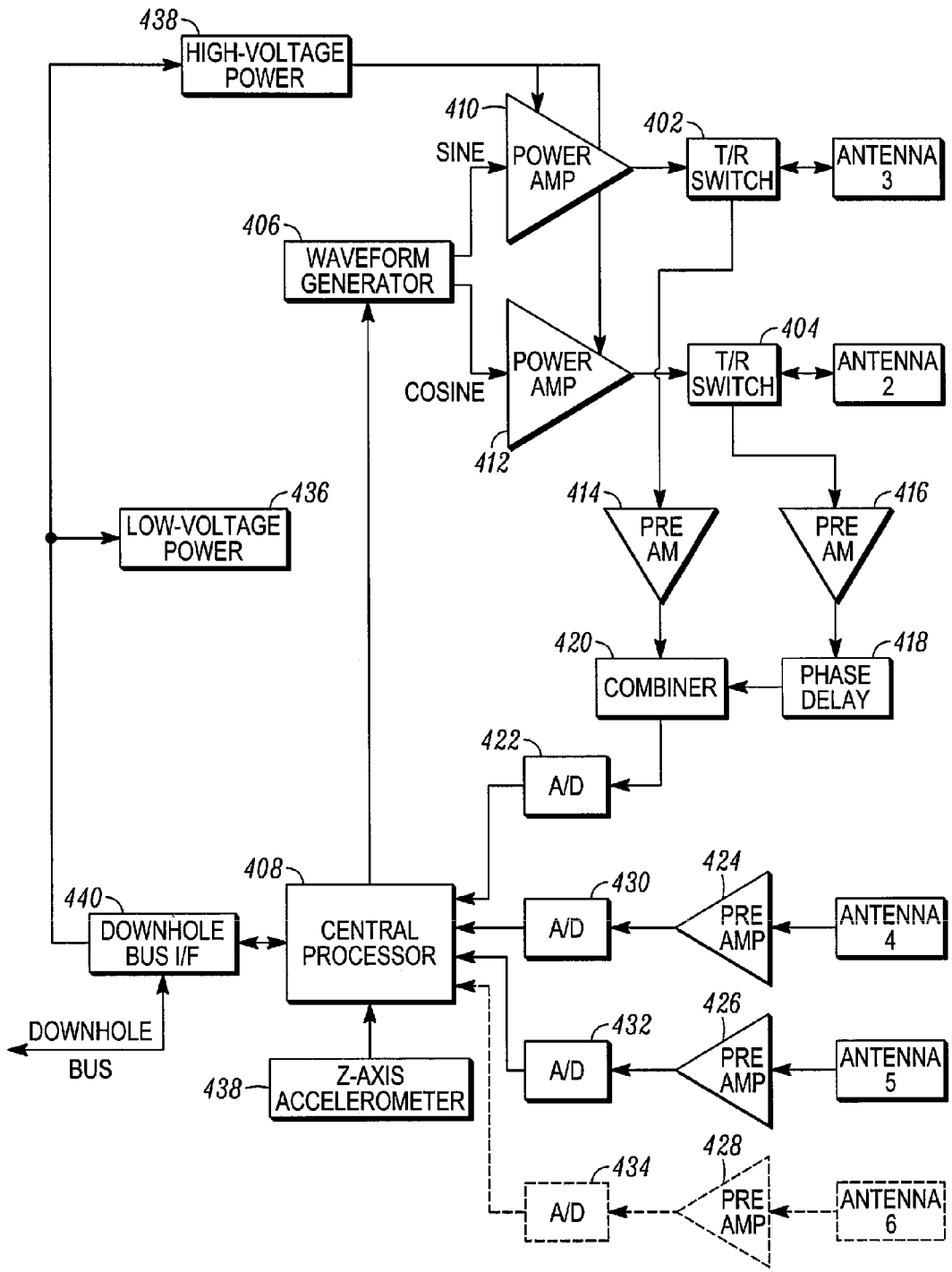
FIG. 4 illustrates an electronic system for exciting the antennas in FIG. 3 according to an embodiment of the present invention.

FIG. 4 illustrates a simplified block diagram of an electronic system for supporting tool 200 according to an embodiment of the present invention. It is expected that the electronic system of FIG. 4 is integrated with tool 200. T/R (Transmit and Receive) switches 402 and 404 allow antennas 3 and 2, respectively, to be operated as transmit antennas or receive antennas. In a transmit mode, waveform generator 406, under control of central processor 408, generates quadrature waveforms, that is, sinusoidal waveforms having a 90° phase difference. These waveforms are represented as sine and cosine in FIG. 4. Power amplifiers 410 and 412 amplify these quadrature waveforms to drive antennas 3 and 2, respectively, when T/R switches 402 and 404 are set to transmit.

When receiving signals via antennas 2 and 3, T/R switches 402 and 404 are set to receive, and pre-amps 414 and 416 amplify the received signals. A 90° phase shift to the output of pre-amp 416 is introduced by phase delay element 418, and the result is added to the output of pre-amp 414 by combiner 420. Analog-to-digital converter A/D 422 digitizes the analog output from combiner 420, and provides the resulting digital signal to central processor 408. In this way, the response of antenna 2 is effectively phase shifted in the time domain by 90° before being added to the response of antenna 3.

Although the phase shift and signal combining may be done in hardware, as shown in FIG. 4 for illustrative purposes, such processing may be implemented after analog-to-digital conversion by digital signal processing (DSP), where the DSP may be realized by software or firmware, running on a programmable processor.

Three more reception pathways are provided for high-resolution antennas 4 through 6, comprising pre-amplifiers 424, 426, and 428, and analog-to-digital converters 430, 432, and 434. Due to the relatively low resonance frequencies involved, all signals may be sampled at full speed, twice the Nyquist rate or higher, enabling the implementation of down-conversion, coherent detection, and decimation on the DSP level.

Components representing analog-to-digital converter 434 and pre-amplifier 428 are shown as dashed to indicate that they are not used in mode B, where antenna 6 is not used.

Other components in the system of FIG. 4, such as low-voltage power supply 436, high-voltage power supply 438, z-axis accelerometer 438, and downhole I/F (Interface) bus 440, are typical components used in electronic systems for well logging. Downhole I/F bus 440 allows communication by a bus, or communication channel, from tool 200 to outside the borehole.

Figure 5:
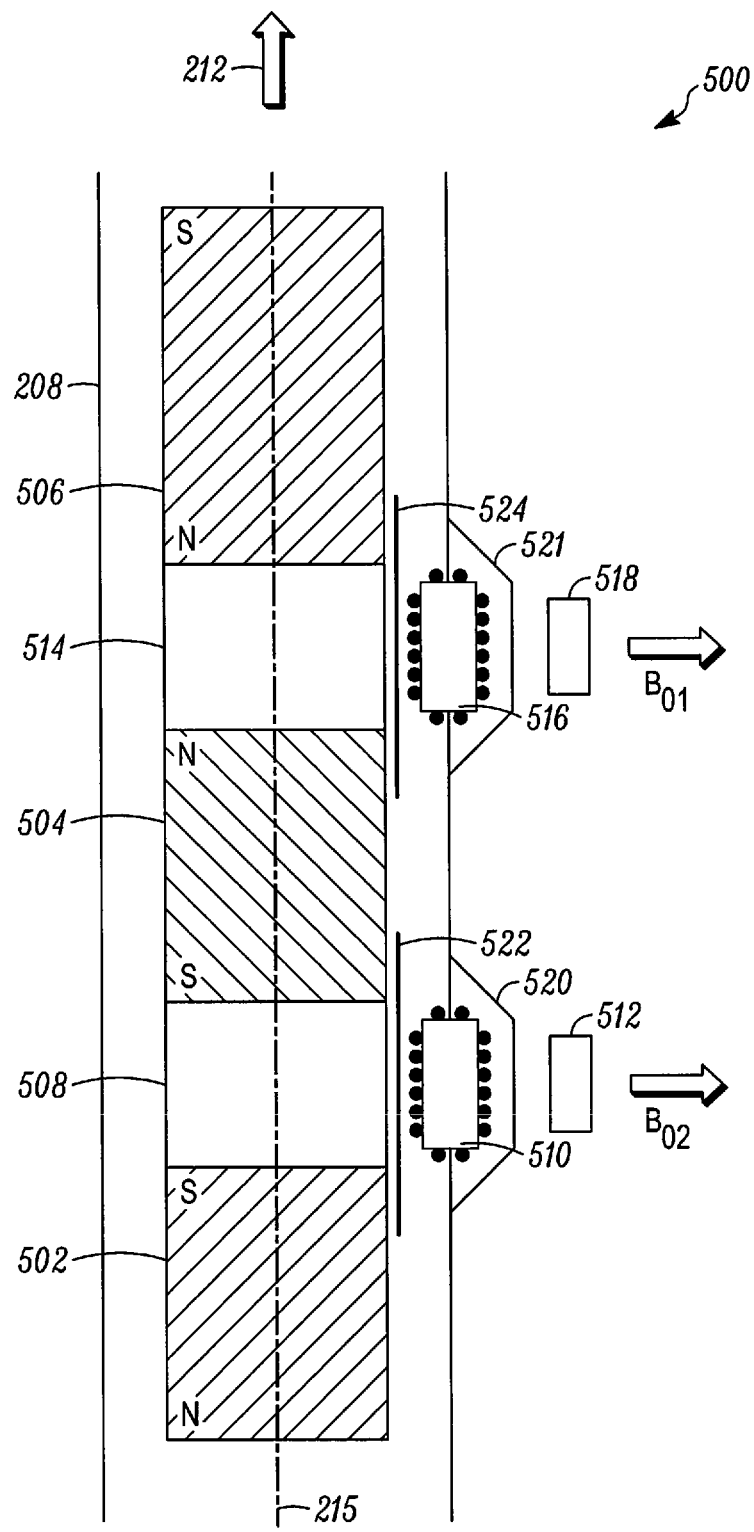
FIG. 5 illustrates another embodiment of the present invention in which two sensitive volumes are created.

FIG. 5 illustrates a cross-sectional, plan view of tool 500 according to another embodiment of the present invention, where three magnets, 502, 504, and 506, are arranged with alternating polarization directions, as shown. Pole pieces 508 and 510 guide magnetic flux from magnets 502 and 504 to sensitive volume 512, where the static magnetic field vector is indicated by $B_{01}$. Pole pieces 514 and 516 guide the magnetic flux from magnets 504 and 506 to sensitive volume 518, where the static magnetic field vector is indicated by $B_{02}$.

Pole pieces 510 and 516 serve as cores for multiple solenoids, as discussed with respect to FIG. 2, and so a detailed description of these solenoids need not be repeated. Again as discussed with respect to FIG. 2, components 520 and 521 are skids, and components 522 and 524 are shields. The electronic system described in FIG. 4 may be duplicated in the embodiment of FIG. 5, so that the solenoids formed around pole piece 510 are driven by one of the electronic systems, and the solenoids formed around pole piece 516 are driven by the other electronic system.

It is expected that tool 500 of FIG. 5, with the use of three magnets to create two sensitive volumes, will provide improvement, when compared to tool 200, in logging speed and (or) virtual independence of logging speed with respect to T1. Magnet 506 is longer than magnets 504 and 502. As a result, the upper volume, sensitive volume 518, follows a relatively long pre-polarization magnet compared to the lower volume, sensitive volume 512, thereby enabling the determination of NMR porosity in sensitive volume 518. The second measurement for the Coates permeability equation, BVI, may be obtained without much pre-polarization. Consequently, the BVI measurement may be performed in the lower volume, taking advantage of the dual role of center magnet 504.

It is possible to show that the arrangement of antennas as shown in FIG. 3 is logically equivalent to an array of vertically stacked solenoids, each ¼ the length of the solenoids in FIG. 3. For example, if the solenoids in FIG. 3 are 12 inches high, then it may be shown that they are logically equivalent to an array of vertically stacked 3-inch solenoids. By delaying and co-adding the signals of these imaginary solenoids, we could (in principle) recover a high-resolution signal with good signal-to-noise properties.

However, there are several good reasons why a physical array of relatively small solenoids is undesirable. Such relatively small solenoids may interfere with each other, and therefore de-tune each other, or otherwise they may be arranged in an overlapping fashion. Neither option is attractive. Furthermore, it is very difficult to recover a lower-resolution signal in low-SNR situations. Ideally, one would start with a low-resolution signal and add detail information to it consistent with the noise level in the input signal.

Ignoring end effects, we may summarize the winding schemes of the logically equivalent array of vertically stacked solenoids in matrix notation by use of the matrix U, where $$U = \begin{matrix} +1 & +1 & +1 & +1 \\ +1 & +1 & -1 & -1 \\ +1 & -1 & -1 & +1 \\ +1 & -1 & +1 & -1 \end{matrix}$$

In the above matrix, we have divided each solenoid into four equal sections (3-inch sections for the case in which the solenoid of FIG. 3 is 12 inches high), and have arranged the solenoids side-by-side. The sign is given by the relationship of a given winding sense to the sense of the transmitter antenna pair of antennas 2 and 3. In other words, the quadrature transmitter establishes an absolute phase reference and the individual sections of the receiver solenoids may pick it up either in-phase (+1) or 180° out of phase (−1).

Another way to view the above description is to consider the transformation y=Ux, where the first component of vector x is the combined response of antennas 2 and 3, the second component is the response of antenna 4, the third component is the response of antenna 5, and the fourth component is the response of antenna 6. The transformed response, y, provides information that is logically equivalent to the array of vertically stacked antennas, as discussed above. To see this, ignore the contribution from antenna 2, which is sensitive to a received magnetic field vector orthogonal to the field vectors in which the other antennas are sensitive, and line up the magnetic directions for antennas 3 through 6 as follows, where a +1 is used instead of (+), and a −1 is used instead of (−).

$$\begin{matrix} +1 & +1 & +1 & +1 \\ +1 & +1 & +1 & +1 \\ +1 & +1 & -1 & -1 \\ +1 & +1 & -1 & -1 \\ +1 & -1 & -1 & +1 \\ +1 & -1 & -1 & +1 \\ +1 & -1 & +1 & -1 \\ +1 & -1 & +1 & -1 \end{matrix} \quad (1)$$

If one weights the above columns by the first row in the matrix by U, and adds, one obtains an imaginary solenoid having the following magnetic directions:

+1
+1
0
0
0
0
0
0.

Because only the first two "windings" are non-zero, this imaginary solenoid is ¼ as high as the original physical solenoid.

Weighting the columns of the array in Eq. (1) by the second row in U, and adding, one obtains a second imaginary solenoid having the following magnetic directions:

0
0
+1
+1
0
0
0
0.

This is seen to be equivalent to a solenoid with ¼ the height of the physical solenoid, but displaced relative to the first displayed imaginary solenoid. Continuing in this way with the third and fourth rows in U, it is seen how the transformation provided by U yields an array of four imaginary solenoids, each with ¼ the resolution of the original physical solenoids.

As stated earlier, other embodiments may be realized in which the magnetic moment directions may be changed, provided the relative relationships of the magnetic moment directions for any one particular solenoid are maintained. For such embodiments, one merely inverts the sign of a column, or columns, in the matrix U when combining the responses of the various antennas. For example, for an embodiment similar to that of FIG. 3, but where now, during a receive mode, the induced current in the top-half section of solenoid 4 is 180° out of phase with respect to the induced current in solenoid 3, the signs of the entries in the second column of U may be inverted, so that the resulting imaginary solenoids provide the same response.

By inspection, $$UU=4I,$$

where I is the four by four identity matrix. That is, U is its own inverse, except for a constant factor. Thus, the columns (or rows) of U form a complete basis set for a unitary transform, which is the Hadamard transform, give or take some reshuffling of matrix columns. Similar to the properties of a Fourier transform, which is also unitary in its symmetric notation, transforming a signal between the spatial and the spatial-frequency domain neither adds nor subtracts noise. That is, applying the transformation y=Ux merely rotates (and scales by a factor of four) the noise vector. As a result, the SNR is not changed.

Figure 1:
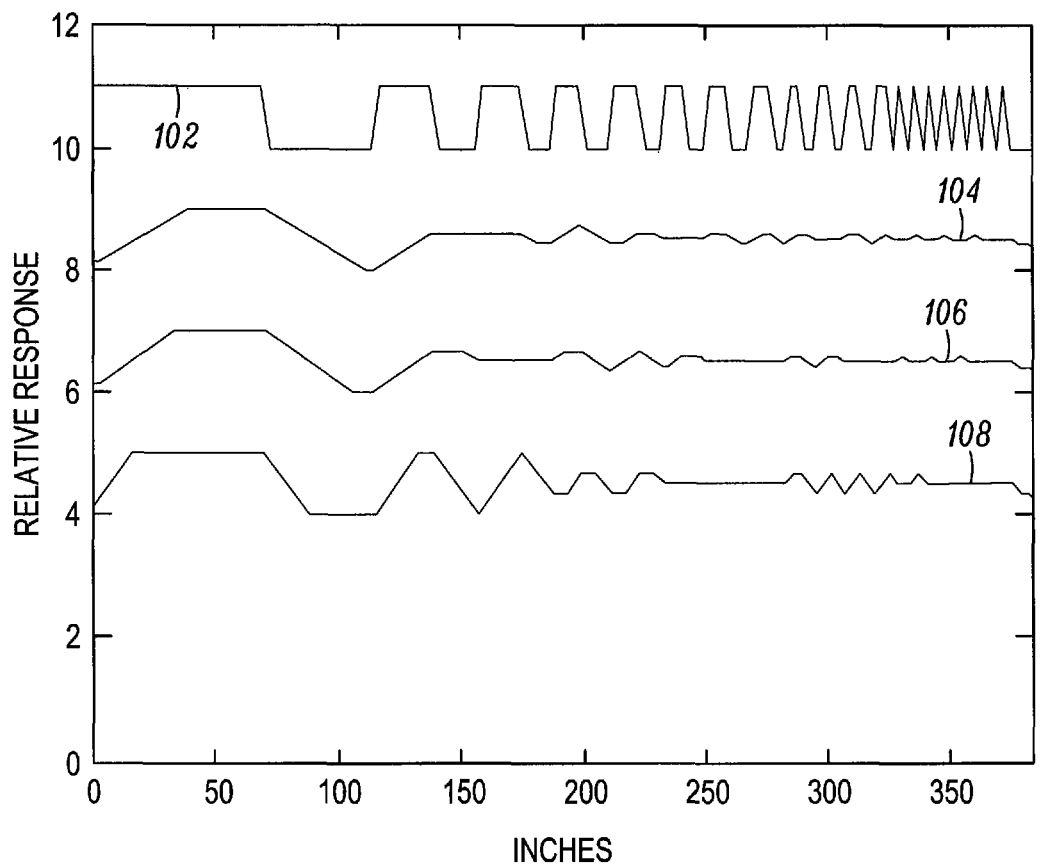
FIG. 1 illustrates antenna responses for prior art NMR logging tools.
Figure 6:
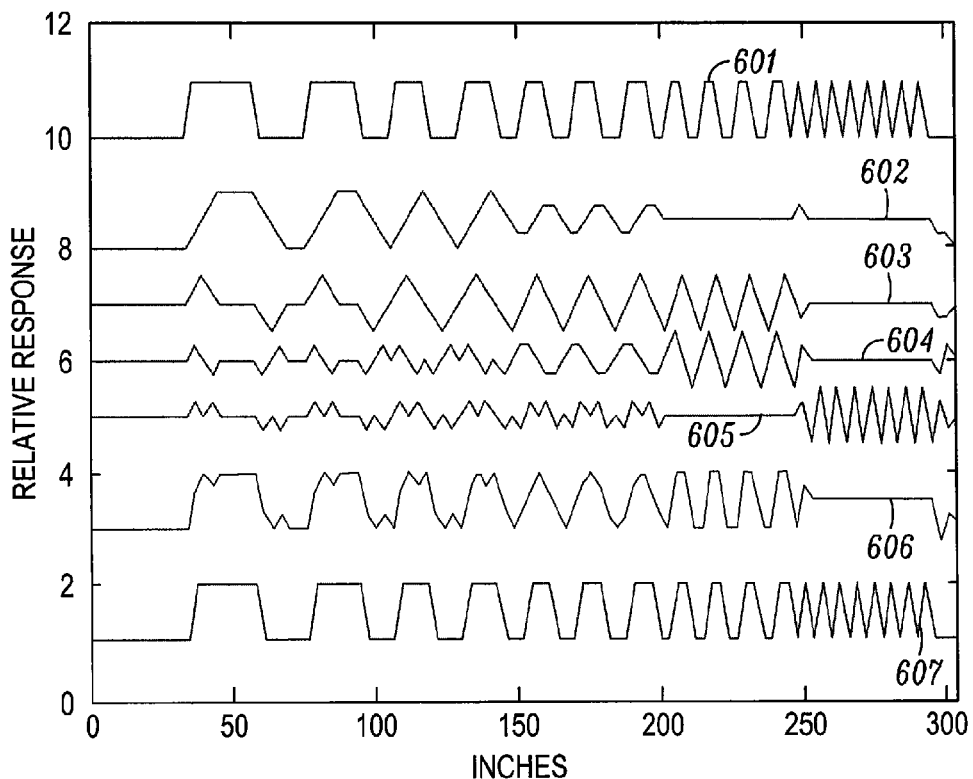
FIG. 6 illustrates simulated antenna responses for an embodiment of the present invention.

These properties may be demonstrated as shown in FIG. 6. Using a chirp signal as in FIG. 1, labeled 601 in FIG. 6, four theoretical antenna responses, labeled 602 through 605, are computed. These responses are computed for solenoids that are 12 inches high. Trace 602 is the response of antennas 2 and 3. Note that as the formation length scale becomes smaller to the right of FIG. 6, the responses of antennas 2 and 3 are sensitive only to an average of the true formation properties, and the contrast between high and low readings is lost. Trace 603 is the response of antenna 4, and trace 604 is the response of antenna 5. Trace 605 is the response of antenna 6.

Trace 606 is the sum of traces 602 through 604. Although not immediately obvious, a fairly good reconstruction of the input chirp signal is achieved. Note that trace 606 shows full amplitude excursions down to the 6-inch scale. There are some Gibbs type glitches, similar to the Gibbs phenomenon associated with performing an inverse Fourier transform after a square window has been applied. Trace 606 corresponds to mode B, where antenna 6 is not used.

Trace 607 is the sum of the traces 602 through 605, corresponding to the mode A of operation in which antenna 6 is used. Note that the input chirp signal is essentially fully recovered, including the 3-inch length scale.

Figure 7:
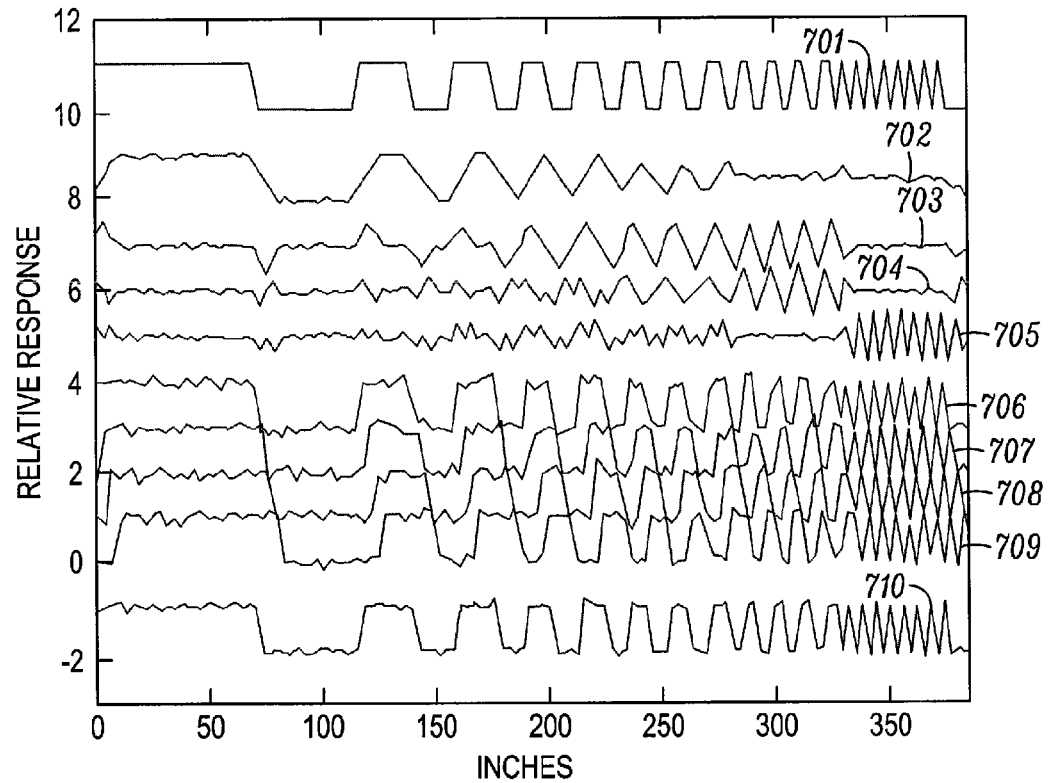
FIG. 7 illustrates simulated antenna responses for an embodiment of the present invention in which simulated thermal noise is added.

FIG. 7 illustrates antenna responses in which a pseudorandom sequence is added to input chirp signal 701 to simulate thermal noise. In this simulation, the logging speed is 60 feet per minute (fpm), sampling is performed every 3 inches, and the pulse rate is 4/sec. This allows for a magnetization time of 0.25 seconds, which is sufficient for BVI measurements, but typically insufficient for porosity measurements.

For FIG. 7, the antenna responses are computed as before, where traces 702 through 705 represent the same antenna responses, except for the simulated noise, as traces 602 through 605, respectively. Running these signals through the matrix U, we obtain traces 706 through 709. These traces are shifted, noisy versions of the input chirp signal.

Re-aligning and adding traces 706-709 yields trace 710. Specifically, traces 706 through 709 are shifted, respectively, by 0, −1, −2, and −3 steps, and then added. Shifting the antenna responses destroys any correlation between noise samples, resulting in a factor-of-two improvement. This may be observed by comparing the SNR and resolution of trace 710 with that of trace 702. Note that the SNR of trace 710 is the same as trace 702, but a much higher resolution has been achieved.

As a caveat we state that the set of parameters used in the simulation of FIG. 7 pays no attention to cycle time limitations due to recovery times. We have assumed a logging speed of 60 fpm, pulsing every 250 ms, and sampling every 3 inches. The baseline comparison should be the BVI-only mode of the CMR tool as shown in trace 108 in FIG. 1. Tool 500 of FIG. 5 approaches, at the expense of complex hardware, the goal of NMR logging without cycle time limitations.

Figure 10:
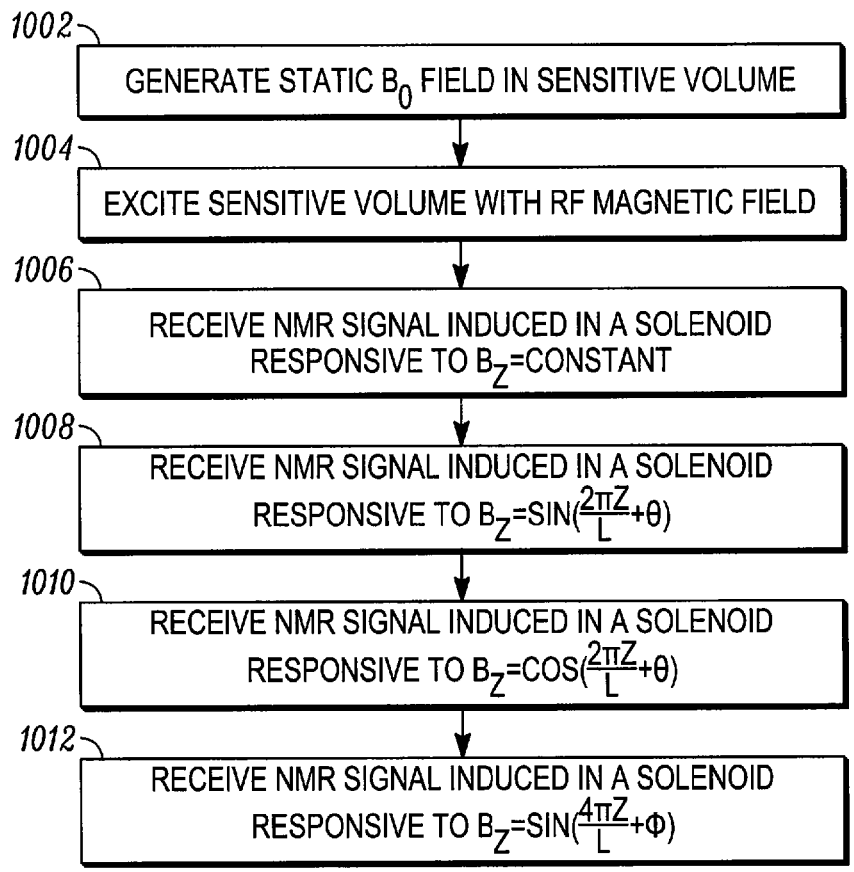
FIG. 10 illustrates a method according to an embodiment of the present invention.

FIG. 10 illustrates a method according to an embodiment. In block 1002, a static magnetic field is generated in a sensitive volume, and in block 1004 the sensitive volume is excited by an RF magnetic field. In block 1006, a received NMR signal is induced in a solenoid having an antenna response that is predominantly sensitive to a magnetic field in the sensitive volume having zero spatial variation in the z-direction of the sensitive volume. In block 1008, another received NMR signal is induced in another solenoid having an antenna response that is predominantly sensitive to a magnetic field in the sensitive volume having a spatial variation with period equal to the solenoid length, where for simplicity, FIG. 10 assumes that each solenoid has the same length L. In block 1010, another received NMR signal is induced in another solenoid having an antenna response that is predominantly sensitive to a magnetic field in the sensitive volume also having a spatial variation with period equal to the solenoid length, but phase shifted 90° relative to that of the previous solenoid. In block 1012, another received NMR signal is induced in another solenoid having an antenna response that is predominantly sensitive to a magnetic field in the sensitive volume having a spatial variation with period equal to one-half the solenoid length.

Various modifications may be made to the disclosed embodiments without departing from the scope of the invention as claimed below. For example, for some embodiments, the various sections, or groups of windings, of the solenoids described above with various phased contributions to the total NMR received signal may be realized without electrically connecting together the various sections, or groups of windings, of a solenoid. The effective relative phases may be realized by analog electronics, or in the digital domain.

For example, consider antenna (solenoid) 4 in FIG. 3. Solenoid 4 may be formed from a top-half solenoid and a bottom-half solenoid, as discussed earlier, each wound in the same direction about axis 209. However, instead of electrically connecting the bottom end of the top solenoid to the bottom end of the bottom solenoid, as discussed earlier, the signals provided by the two solenoids during reception may be combined by an RF combiner after a 90° phase shift has been applied to the output of the bottom solenoid.

Continuing with this example, in another implementation, the RF signals provided by the top and bottom solenoids may be down-converted to an intermediate frequency signal, or a base-band signal, each having in-phase and quadrature components, and a 90° phase shift may be introduced into the signal from the bottom solenoid by changing the sign of (phase shifting by 180°) its quadrature component. In yet another implementation, the RF signals provided by the top and bottom solenoids may be down-converted, followed by sampling, to provide complex (in-phase and quadrature components) numbers, so that the 90° phase shift may be implemented in the digital domain by changing the sign of the imaginary (quadrature) component of the signal from the bottom solenoid. Note that in considering these examples, the notion of a solenoid is generalized, so that not all windings of a solenoid are electrically connected form one electrical coil.

However, as discussed earlier, it is suggested that the solenoids should be constructed so as to minimize mutual coupling among the solenoids, and as discussed earlier, this feature may be realized by following the relative winding directions as suggested in FIG. 3, so that each solenoid is composed of a single wire, where the winding sense reverses direction when traversing from one section to an adjacent section as indicated in FIG. 3.

Figure 8:
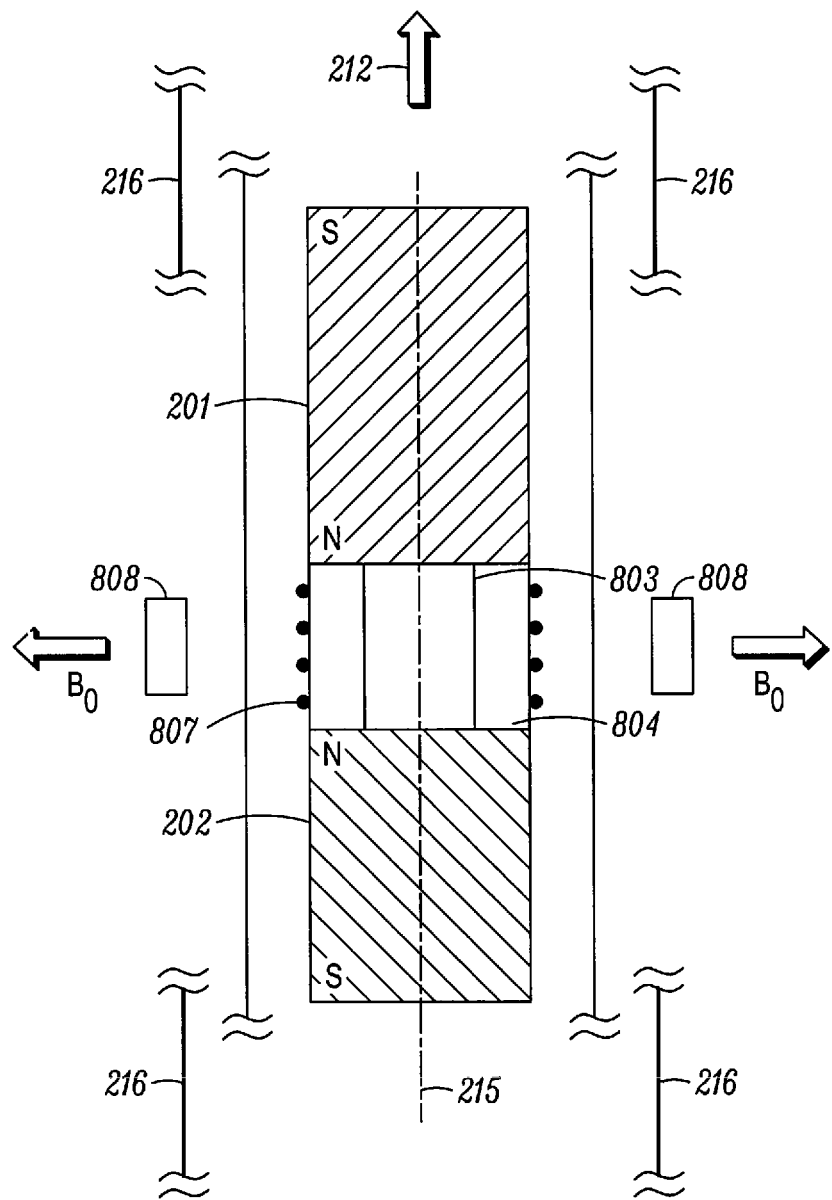
FIG. 8 illustrates an NMR logging tool according to an embodiment of the present invention.

In other embodiments, the position of pole 204 relative to magnets 201 and 202 may be different from that of FIG. 2. One such embodiment is illustrated in FIG. 8, which illustrates a plan view of an embodiment, where pole piece 803 serves a similar function as that of pole piece 203, and pole piece 804 has solenoids formed about it, illustrated in simple fashion by dots 807. Pole piece 804 is cylindrical in shape, with a core for accepting pole piece 803. Pole piece 803 is also cylindrical. Note that pole piece 804 is in-between and adjacent to magnets 201 and 202.

Forming solenoids about pole piece 804 that correspond to solenoids 3, 4, 5, 6 in FIG. 2 is similar to the embodiment of FIG. 2, except that the turns of wire (conductor) are circular in shape as opposed to rectangular. However, the winding of a solenoid about pole piece 804 corresponding to solenoid 2 is done differently because there is no space between the top and bottom faces of pole piece 804 and magnets 201 and 202. Such a longitudinal oriented solenoid may be formed on the outer cylindrical surface of pole piece 804, forming a saddle-shaped solenoid.

Figure 9:
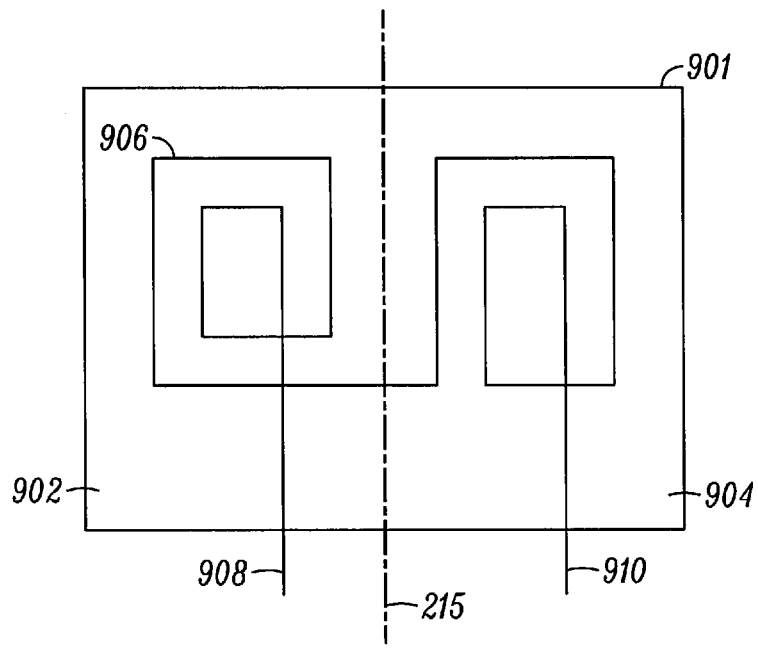
FIG. 9 illustrates a solenoid in the embodiment of FIG. 8.

This may be visualized by referring to FIG. 9, in which pole piece 804 is un-wrapped into plane 901, so that half 902 is the left half-side, relative to axis 215, of pole piece 804 and half 904 is the right half-side of pole piece 804. Solenoid 906 is one wire, with ends at 908 and 910, and comprises two turns on half 902 and two turns on half 904. When wrapped back into a cylindrical shape, solenoid 906 serves a similar function as solenoid 2, generating in the formation a radially directed magnetic field.

Referring to FIG. 8, because of the cylindrical symmetry of the tool, the sensitive volume is a cylindrical annulus, with an inner radius and an outer radius. Within the plane view of FIG. 8, the sensitive volume is labeled 808, where the radially directed static magnetic field is denoted as $B_0$.

For other embodiments, the shape of pole piece 804 need not be cylindrical, and may be integrated with pole piece 803 so that only one pole piece is employed between magnets 201 and 202.

Figure 11:
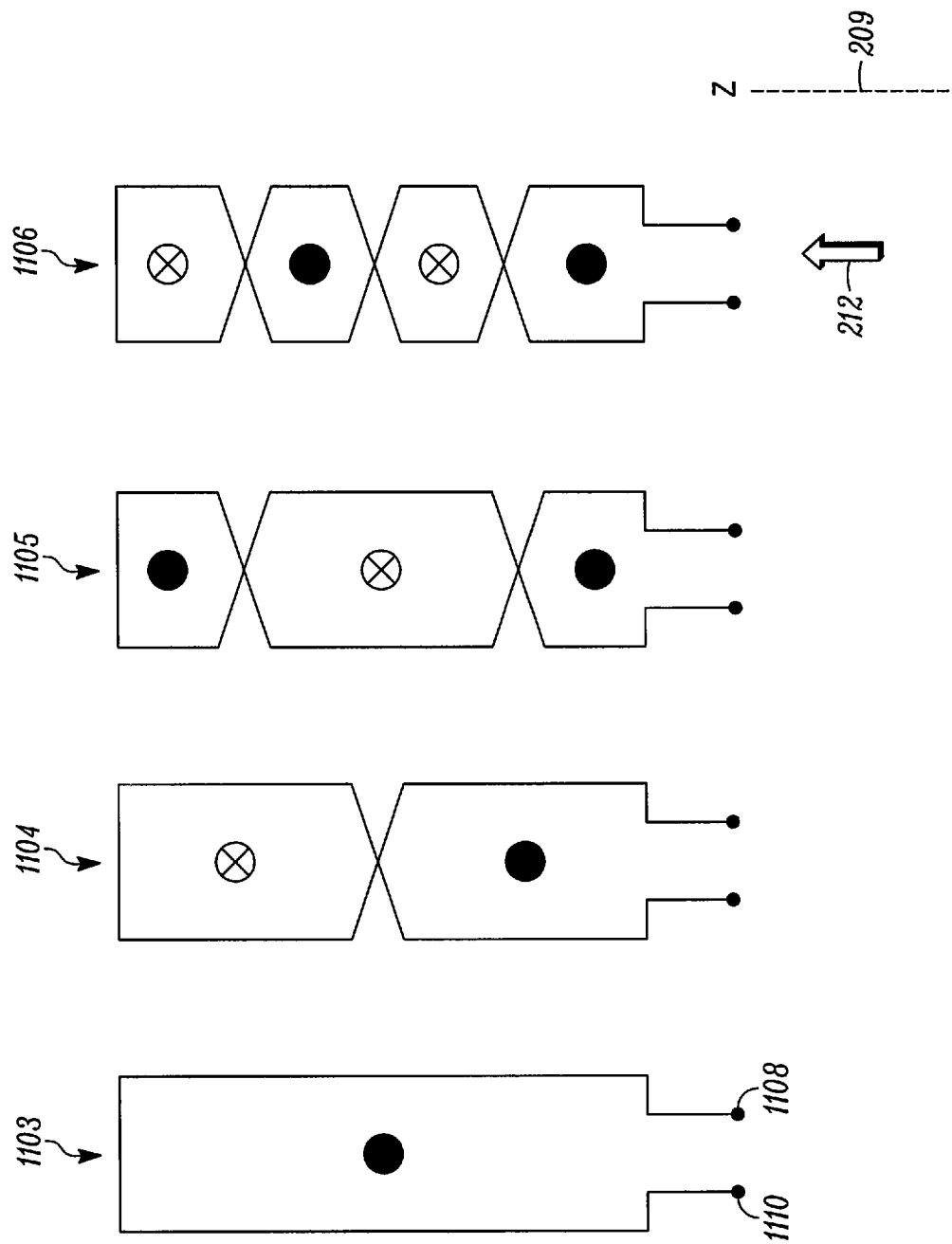
FIG. 11 illustrates another embodiment of the present invention.

For other embodiments, antenna elements other than solenoids may be used. For example, frame-type receive antennas may be employed, as illustrated in FIG. 11. Each antenna comprises wire that is wound about a pole piece. The wire may be wound so as to be curved about a cylindrical pole piece, or planar about a rectangular pole piece, for example. The antennas may be wound about both sides of a pole piece, resulting in a saddle-shaped antenna, as discussed earlier. For ease of discussion, the embodiment illustrated in FIG. 11 comprises planar type windings, and for simplicity, only one winding is shown.

Antennas 1103, 1104, 1105, and 1106 are, roughly speaking, the counterparts to antennas 3, 4, 5, and 6 of FIG. 3. The relationships between the windings of the antennas of FIG. 11 are indicated by the dots and crosses shown in FIG. 11, where a dot denotes a direction pointing out of the drawing sheet, and a cross is a direction pointing into the drawing sheet, as is customary for indicating field vector directions. These directions may be viewed as the relative directions of a magnetic moment.

For example, antenna 1103 comprises one winding of wire, essentially wound as a rectangle. If antenna 1103 were used as a transmit antenna, with a steady direct current entering port 1108 and exiting port 1110, then the magnetic field vector at a position in the plane defined by 1103 would point out of the drawing sheet, as indicated by the solid dot within antenna 1103. Antenna 1103, as a receiving antenna, is predominantly sensitive to a magnetic field in a sensitive volume that has zero spatial variation along z direction 209.

Likewise, if a DC current were to enter at the right side port of each shown antenna and exit at left side port, then the directions of the magnetic moments are indicated as shown in FIG. 11. The magnitude of the magnetic moment for the middle section of antenna 1105 is twice that of the other two sections of antenna 1105. The dominant Fourier components of the antenna responses for the antennas of FIG. 11 are the same as their corresponding antennas in FIG. 3. In the sensitive volume, the magnetic field vector direction to which the receive antennas are responsive have a direction radial to axis 209. Also, as for the antennas of FIG. 3, the antennas in FIG. 11 have zero (in the ideal case) mutual coupling.

The described embodiments have shown the static field vector to have a radial direction relative to axis 209. For some embodiments, the static field vector may have other directions, such as a vertically oriented direction.

The illustration of the antennas in FIG. 11 is not meant to imply a spatial ordering of the antennas in an embodiment. That is, antenna 1104 is not necessarily wound about pole piece 204 after antenna 1103 has been wound about pole piece 204; antenna 1105 is not necessarily wound about pole piece 204 after antenna 1104 has been wound; and so forth.

Figure 12:
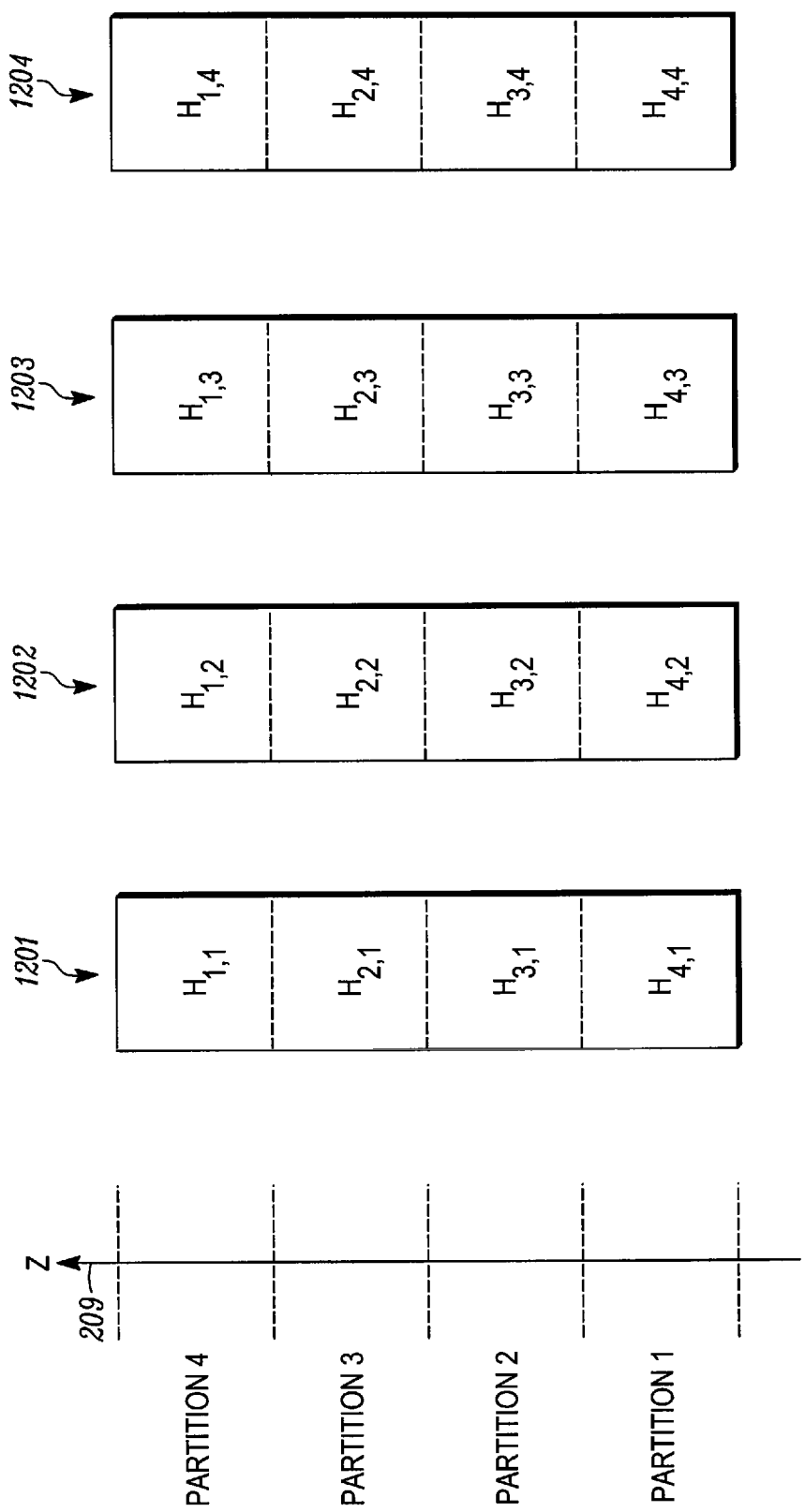
FIG. 12 illustrates an embodiment of the present invention.

The embodiments illustrated in FIGS. 3 and 11 may be abstracted to the embodiment illustrated in FIG. 12. Illustrated in FIG. 12 are four receive antennas, labeled 1201 through 1204. Each antenna is partitioned into four partitions. In implementation, each row of partitions overlap in physical dimension, indicated by z-axis 209, where the partitions are labeled as partition 1 through partition 4. The relative positions of the partitions as shown in FIG. 12 may be viewed as corresponding to positions (row number, column number) of components in a 4 by 4 matrix, so that each partition may be identified by an ordered pair (i, j). In each partition is written a component of a Hadamard matrix H, where the component in the $i^{th}$ row and $j^{th}$ column of H is denoted as $h_{i,j}$, so that corresponding to partition (i, j) is the Hadamard component $h_{i,j}$.

The value $h_{i,j}$ for partition (i, j), up to some scale factor, indicates the partition's contributing magnetic moment when a direct current flows through its corresponding antenna. A partition, as discussed in reference to FIG. 12, is not necessarily a section, as discussed in reference to FIG. 3 or 11. For example, if antenna 1201 is identified with antenna 3 or antenna 1103 of FIGS. 3 and 11, respectively, then each partition in antenna 1201 is simply a part of the single section of antennas 3 or 1103. That is, the union of the partitions in antenna 1201 corresponds to the single section of antennas 3 or 1103. A partition does not necessarily imply a distinct physical structure.

As a particular example, the first column of H may be all ones, where $h_{1,1}=h_{2,1}=h_{3,1}=h_{4,1}=1$, so that each partition in antenna 1201 contributes a magnetic moment in the same direction and with the same magnitude. As another example, the third column of H may be $h_{1,3}=h_{4,3}=1$ and $h_{2,3}=h_{3,3}=-1$, so that antenna 1203 corresponds to antennas 5 and 1105 of FIG. 3 or 11, respectively, where partition 4 of antenna 1203 corresponds to the top section of antennas 5 or 1105, the union of partitions 2 and 3 of antenna 1203 corresponds to the middle section of antennas 5 or 1105, and partition 1 of antenna 1203 corresponds to the bottom section of antennas 5 or 1105.

By considering the above particular examples relating the antennas of FIG. 12 to those of FIGS. 3 and 11, a little thought will show that the flux linkage in a particular antenna due to an injected current in another antenna is given by the dot product of their corresponding columns of the Hadamard matrix H. Because H is constructed to have orthogonal columns, the flux linkage in any one antenna due to current injected in another antenna is zero, thereby resulting in zero mutual coupling. Because the Hadamard matrix may be written so that $H^T=H$, the above discussion could have switched the roles of columns and rows.

Furthermore, because $HH^T=4I_4$, where $I_4$ is the 4 by 4 identity matrix, H is also a unitary matrix, up to a scale factor. Consequently, the received signals generated by antennas 1201 through 1204 may be processed by a unitary transformation to un-mix the response, so that the resolution corresponds to the physical dimension of a partition, that is ¼ of the length of the antennas. Because a unitary transformation merely rotates a noise vector, the SNR is not decreased by the unitary transformation.

The magnetic moments of any particular antenna may be related to a column (or row) of a Hadamard matrix by a scale factor. Accordingly, the embodiment illustrated in FIG. 12 may be generalized as follows. Denote the magnetic moment for partition (i, j) as $m_{i,j}$, and consider the magnetic moment matrix M, where the (i, j) component of M is $m_{i,j}$. Then, the magnetic moments may be related to a Hadamard matrix by M=HD, where D is a diagonal matrix with non-zero, real diagonals. The flux linkage in partition (i, j) due to a current injected in the antenna having partitions (k,l), k=1, 2, . . . , 4, where l≠j, is proportional to the product $m_{i,l}m_{i,j}$. From the orthogonality of the columns of H, it follows that the flux linkage in an antenna due to current in another antenna is zero.

The illustration of the antennas in FIG. 12 is not meant to imply a spatial ordering of the antennas in an embodiment. That is, antenna 1202 is not necessarily wound about pole piece 204 after antenna 1201 has been wound about pole piece 204; antenna 1203 is not necessarily wound about pole piece 204 after antenna 1202 has been wound; and so forth.

Hadamard matrices of higher order may be constructed as follows, $$H_1 = [1],$$
$$H_2 = \begin{bmatrix} 1 & 1 \\ 1 & -1 \end{bmatrix},$$

and $$H_{2^k} = \begin{bmatrix} H_{2^{k-1}} & H_{2^{k-1}} \\ H_{2^{k-1}} & -H_{2^{k-1}} \end{bmatrix},$$

where $2 \leq k$ and k is an integer. The orthogonality property is $H_n H_n^T = nI_n$, where $I_n$ is the n by n identity matrix, where $n=2^k$. Accordingly, although the disclosed embodiments were discussed with respect to four receive antennas, they are easily generalized to systems employing a power of 2 number of receive antennas. Furthermore, because of the way in which the Hadamard matrices are constructed, the four receive antenna embodiment may be viewed as a subset of higher order systems.

Generalizing to higher order systems, an embodiment may comprise n antennas, where $n=2^k$, where k is an integer equal to or greater than 2, where each antenna may be partitioned into n partitions, where each partition may be placed in one-to-one correspondence with an ordered pair (i, j) where i and j are integers ranging from 1 to n. For the range of i and j, a partition corresponding to the ordered pair (i, j) provides a magnetic moment $m_{i,j}$ when a direct current flows through its corresponding antenna. Let $M_n$ denote an n by n magnetic moment matrix with (i, j) component equal to $m_{i,j}$. Then, the magnetic moments may be related to the Hadamard matrix $H_n$ by $$M_n = H_n D_n,$$

where $D_n$ is an n by n diagonal matrix with non-zero, real diagonal elements.

The flux linkage in partition (i, j) due to a current injected in the antenna having partitions (k,l), k=1, 2, . . . , n, where l≠j, is proportional to the product $m_{i,l}m_{i,j}$. Because of the orthogonality property of the columns of $H_n$, the flux linkage in an antenna due to injected current in another antenna is zero.

The columns in the Hadamard matrix $H_n$ may be interchanged without affecting the zero mutual coupling property. This amounts to re-arranging the spatial ordering of the antennas in FIG. 12 (generalized to order n) about a pole piece. However, because the drawings are not meant to specify a particular spatial ordering of the antennas about a pole piece, so that other embodiments may have the antennas formed about a pole piece with different orderings, stating that the columns in $H_n$ may be interchanged is somewhat redundant.

In the claims, various mathematical relationships may be used to describe relationships among one or more quantities. For example, a mathematical relationship or mathematical transformation may express a relationship by which a quantity is derived from one or more other quantities by way of various mathematical operations, such as addition, subtraction, multiplication, division, etc. Or, a mathematical relationship may indicate that a quantity is larger, smaller, or equal to another quantity. These relationships and transformations are in practice not satisfied exactly, and should therefore be interpreted as "designed for" relationships and transformations. One of ordinary skill in the art may design various working embodiments to satisfy various mathematical relationships or transformations, but these relationships or transformations can only be met within the tolerances of the technology available to the practitioner. The term "substantially" may be used in a claim to reflect this fact.

Accordingly, in the following claims, it is to be understood that claimed mathematical relationships or transformations can in practice only be met within the tolerances or precision of the technology available to the practitioner, and that the scope of the claimed subject matter includes those embodiments that substantially satisfy the mathematical relationships or transformations so claimed.

What is claimed is:

1. A well logging tool comprising:
   a first antenna having an antenna response, the first antenna response having a Fourier series expansion along a spatial dimension of length L, the Fourier series expansion of the first antenna response having a largest-in-magnitude Fourier component with zero spatial-frequency; and
   a second antenna having length L and an antenna response, the second antenna response having a Fourier series expansion along the spatial dimension of length L, the Fourier series expansion of the second antenna response having a largest-in-magnitude Fourier component with period L.

2. The well logging tool as set forth in claim 1, wherein the first antenna comprises a first solenoid having an axis, and the second antenna comprises a second solenoid having an axis co-linear with the axis of the first solenoid.

3. The well logging tool as set forth in claim 1, further comprising:

a first magnet;
a second magnet, wherein the first and second magnets are oriented to have substantially opposing magnetic orientations; and
a pole piece to guide the magnetic fields of the first and second magnets.

4. The well logging tool as set forth in claim 3, further comprising:
a third magnet oriented to have an opposing magnetic orientation with respect to the second magnet; and
a second pole piece to guide the magnetic fields of the second and third magnets.

5. The well logging tool as set forth in claim 3, further comprising:
a second pole piece, wherein the first and second antennas are formed around the second pole piece.

6. The well logging tool as set forth in claim 5, further comprising:
a third magnet oriented to have an opposing magnetic orientation with respect to the second magnet; and
a third pole piece to guide the magnetic fields of the second and third magnets.

7. The well logging tool as set forth in claim 1, further comprising:
a pole piece, wherein the first antenna comprises a solenoid formed around the pole piece, and the second antenna comprises a solenoid formed around the pole piece.

8. The well logging tool as set forth in claim 7, wherein the pole piece is adjacent to the first and second magnets.

9. The well logging tool as set forth in claim 1, further comprising:
a third antenna having length L and an antenna response, the third antenna response having a Fourier series expansion along the spatial dimension of length L, the Fourier series expansion of the third antenna response having a largest-in-magnitude Fourier component with period L and with a phase shift of 90° relative to the largest-in-magnitude Fourier component of the second antenna response.

10. The well logging tool as set forth in claim 9, wherein the first, second, and third antennas comprise, respectively, first, second, and third solenoids, each with co-linear axes.

11. The well logging tool as set forth in claim 9, further comprising:
a fourth antenna having length L and an antenna response, the fourth antenna response having a Fourier series expansion along the spatial dimension of length L, the Fourier series expansion of the fourth antenna response having a largest-in-magnitude Fourier component with period L/2.

12. The well logging tool as set forth in claim 11, further comprising:
a first magnet;
a second magnet, wherein the first and second magnets are oriented to have opposing magnetic orientations; and
a pole piece to guide the magnetic fields of the first and second magnets.

13. The well logging tool as set forth in claim 12, wherein the first, second, third, and fourth antennas are, respectively, first, second, third, and fourth solenoids each formed around the pole piece.

14. The well logging tool as set forth in claim 12, further comprising a second pole piece, where the first, second, third, and fourth antennas are, respectively, first, second, third, and fourth solenoids each formed around the second pole piece.

15. A well logging tool comprising:
a first antenna; and
a second antenna comprising a first section and a second section, where magnetic flux linkage in the first section due to a first current in the first antenna is substantially equal to the negative of magnetic flux linkage in the second section due to the first current in the first antenna.

16. The well logging tool as set forth in claim 15, wherein the sum of the magnetic flux linkages in the first and second sections of the second antenna, divided by a self magnetic flux linkage in the first antenna due to the first current in the first antenna, is less than −10 dB.

17. The well logging tool as set forth in claim 15, further comprising:
a first magnet having an axial magnetization; and
a second magnet having an axial magnetization oppositely oriented with respect to the first magnet.

18. The well logging tool as set forth in claim 15, further comprising:
a third antenna comprising a first section, a second section, and a third section;
where for the first current in the first antenna, magnetic flux linkage in the first section of the third antenna is substantially equal to magnetic flux linkage in the third section of the third antenna, and is substantially equal to the negative of one-half of magnetic flux linkage in the second section of the third antenna; and
where for a second current in the second antenna, magnetic flux linkage in the first section of the third antenna is substantially equal to the negative of magnetic flux linkage in the third section of the third antenna, and magnetic flux linkage in the second section of the third antenna is zero.

19. The well logging tool as set forth in claim 18, wherein
the sum of the magnetic flux linkages in the first and second sections of the second antenna, divided by a self magnetic flux linkage in the first antenna due to the first current in the first antenna, is less than −10 dB;
the sum of the magnetic flux linkages in the first, second, and third sections of the third antenna due to the first current in the first antenna, divided by the self magnetic flux linkage in the first antenna, is less than −10 dB; and
the sum of the magnetic flux linkages in the first, second, and third sections of the third antenna due to the second current in the second antenna, divided by a self magnetic flux linkage in the second antenna due to the second current in the second antenna, is less than −10 dB.

20. The well logging tool as set forth in claim 18, further comprising:
a first magnet having an axial magnetization; and
a second magnet having an axial magnetization oppositely oriented with respect to the first magnet.

21. The well logging tool as set forth in claim 18, further comprising a pole piece, wherein
the first antenna comprises windings wound around the pole piece in a same direction;
the second antenna comprises a first set of windings and a second set of windings, wherein the first and second set of windings of the second antenna are wound around the pole piece in opposite directions with respect to each other; and
the third antenna comprises a first set of windings, a second set of windings, and a third set of windings, where the first and third sets of windings of the third antenna are each wound around the pole piece in opposite direction with respect to the second set of windings of the third antenna.

22. The well logging tool as set forth in claim 18, further comprising:

a fourth antenna comprising a first section, a second section, a third section, and a fourth section;

where for the first current in the first antenna, magnetic flux linkages in the first and third sections of the fourth antenna are equal to each other, and magnetic flux linkages in the second and fourth sections of the fourth antenna are equal to each other and opposite in sign to the magnetic flux linkages in the first and third sections of the fourth antenna.

23. The well logging tool as set forth in claim 22, wherein the sum of the magnetic flux linkages in the first and second sections of the second antenna, divided by a self magnetic flux linkage in the first antenna due to the first current in the first antenna, is less than −10 dB;

the sum of the magnetic flux linkages in the first, second, and third sections of the third antenna due to the first current in the first antenna, divided by the self magnetic flux linkage in the first antenna, is less than −10 dB;

the sum of the magnetic flux linkages in the first, second, and third sections of the third antenna due to the second current in the second antenna, divided by a self magnetic flux linkage in the second antenna due to the second current in the second antenna, is less than −10 B; and the sum of the magnetic flux linkages in the first, second, third, and fourth sections of the fourth antenna due to the first current in the first antenna, divided by the self magnetic flux linkage in the first antenna, is less than −10 dB.

24. The well logging tool as set forth in claim 22, further comprising a pole piece, the fourth antenna comprising a first set of windings, a second set of windings, a third set of windings, and a fourth set of windings, wherein the first and third sets of windings of the fourth antenna are wound around the pole piece in a same direction, and the second and fourth sets of windings of the fourth antenna are each wound around the pole piece in opposite direction with respect to the first and third sets of windings of the fourth antenna.

25. The well logging tool as set forth in claim 15, further comprising:

a third magnet having an axial magnetization oppositely oriented with respect to the second magnet.

26. An apparatus comprising:

n antennas, where $n=2^k$, where k is an integer equal to or greater than 2, where each antenna may be partitioned into n partitions, each partition in one-to-one correspondence with an ordered pair (i, j) where i and j are integers ranging from 1 to n, where for the range of i and j, a partition corresponding to the ordered pair (i, j) provides a magnetic moment $m_{ij}$ when a direct current flows through its corresponding antenna, where for an n by n magnetic moment matrix $M_n$ with component (i,j) equal to $m_{ij}$, $M_n = H_n D_n$, where H is an n by n Hadamard matrix and $D_n$ is an n by n diagonal matrix with non-zero, real diagonal elements.

27. The apparatus as set forth in claim 26, where flux linkage in partition (i, j) due to a current injected in the antenna having partitions (k,l), k=1, 2, . . . , n, where l≠j, is proportional to the product $m_{i,l} m_{i,j}$.

28. The apparatus as set forth in claim 27, further comprising:

a first magnet having an axial magnetization; and a second magnet having an axial magnetization oppositely oriented with respect to the first magnet.

29. The apparatus as set forth in claim 26, further comprising:

a first magnet having an axial magnetization; and a second magnet having an axial magnetization oppositely oriented with respect to the first magnet.

30. A method to measure the nuclear magnetic response of a sensitive volume in a formation, the sensitive volume having a z-direction, the method comprising:

generating a static magnetic field in the sensitive volume;

receiving a magnetic resonance signal induced in a first antenna having an antenna response predominantly sensitive to a time-varying magnetic field vector in the sensitive volume with zero spatial variation along the z-direction; and receiving a magnetic resonance signal induced in a second antenna having a length and having an antenna response predominantly sensitive to a time-varying magnetic field vector in the sensitive volume spatially varying in the z-direction with a period equal to the length of the second antenna.

31. The method as set forth in claim 30, further comprising:

receiving a magnetic resonance signal induced in a third antenna having a length and having an antenna response predominantly sensitive to a time-varying magnetic field vector in the sensitive volume spatially varying in the z-direction with a period equal to the length of the third antenna, and having a phase shift of 90° relative to the antenna response of the second antenna.

32. The method as set forth in claim 31, further comprising:

receiving a magnetic resonance signal induced in a fourth antenna having a length and having an antenna response predominantly sensitive to a time-varying magnetic field vector in the sensitive volume spatially varying in the z-direction with a period equal to one-half the length of the fourth antenna.

* * * * *

UNITED STATES PATENT AND TRADEMARK OFFICE
CERTIFICATE OF CORRECTION

PATENT NO. : 8,421,454 B2  Page 1 of 1
APPLICATION NO. : 12/513792
DATED : April 16, 2013
INVENTOR(S) : Prammer et al.

It is certified that error appears in the above-identified patent and that said Letters Patent is hereby corrected as shown below:

In the Claims:

In column 23, line 24, in Claim 23, delete "-10 B;" and insert -- -10 dB;--, therefor In column 23, line 50, in Claim 26, delete "$m_{ij}$" and insert --$m_{i,j}$--, therefor In column 24, line 3, in Claim 26, delete "$m_{ij}$" and insert --$m_{i,j}$--, therefor Signed and Sealed this
Twenty-sixth Day of November, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,421,454 B2  
APPLICATION NO. : 12/513792  
DATED : April 16, 2013  
INVENTOR(S) : Prammer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 790 days.

Signed and Sealed this
Eighth Day of September, 2015

Michelle K. Lee
*Director of the United States Patent and Trademark Office*